US010093642B2

(12) United States Patent
Botta et al.

(10) Patent No.: US 10,093,642 B2
(45) Date of Patent: Oct. 9, 2018

(54) MULTITARGET HEDGEHOG PATHWAY INHIBITORS AND USES THEREOF

(71) Applicants: UNIVERSITA' DEGLI STUDI DI SIENA, Siena (SI) (IT); UNIVERSITA' DEGLI STUDI DI ROMA "LA SAPIENZA", Rome (RM) (IT)

(72) Inventors: Bruno Botta, Rome (IT); Alberto Gulino, Rome (IT); Maurizio Botta, Siena (IT); Mattia Mori, Rome (IT); Lucia Di Marcotullio, Rome (IT); Paola Infante, Rome (IT); Francesca Ghirga, Rome (IT); Sara Toscano, Rome (IT); Cinzia Ingallina, Rome (IT); Romina Alfonsi, Rome (IT)

(73) Assignees: UNIVERSITÀ DEGLI STUDI DI ROMA "LA SAPIENZA", Rome (RM) (IT); UNIVERSITA DEGLI STUDI DI SIENA, Siena (SI) (IT)

( * ) Notice: Subject to any disclaimer, the term of this patent is extended or adjusted under 35 U.S.C. 154(b) by 0 days.

(21) Appl. No.: 14/898,955

(22) PCT Filed: Jun. 25, 2014

(86) PCT No.: PCT/EP2014/063449
§ 371 (c)(1),
(2) Date: Dec. 16, 2015

(87) PCT Pub. No.: WO2014/207069
PCT Pub. Date: Dec. 31, 2014

(65) Prior Publication Data
US 2016/0368886 A1    Dec. 22, 2016

(30) Foreign Application Priority Data

Jun. 25, 2013  (IT) .............................. RM2013A0366

(51) Int. Cl.
*C07D 311/34* (2006.01)
*A61K 9/00* (2006.01)
(Continued)

(52) U.S. Cl.
CPC .......... *C07D 311/34* (2013.01); *A61K 9/0019* (2013.01); *A61K 9/127* (2013.01);
(Continued)

(58) Field of Classification Search
CPC .... C07D 311/34; A61K 9/0019; A61K 9/127; A61K 31/121; A61K 31/343; A61K 31/35; A61K 31/352; A61K 45/06
(Continued)

(56) References Cited

U.S. PATENT DOCUMENTS

| 5,002,603 A | 3/1991 | Safir et al. |
| 2004/0147551 A1* | 7/2004 | Heaton ................ C07D 311/26 514/312 |

(Continued)

FOREIGN PATENT DOCUMENTS

| CN | 102697768 | * 10/2012 |
| WO | WO2009026657 | * 3/2009 |

OTHER PUBLICATIONS

Liu; Chin J Cancer 2011, 3,0 13-26.*
(Continued)

*Primary Examiner* — Daniel R Carcanague
(74) *Attorney, Agent, or Firm* — Lucas & Mercanti, LLP

(57) ABSTRACT

The present invention concerns compounds that selectively inhibit the activity of the Hedgehog (Hh) pathway, their preparation and uses thereof. The compounds of the present invention are useful in treating Hh-dependent tumors, such as medulloblastoma (MB).

6 Claims, 15 Drawing Sheets

Figure 1:
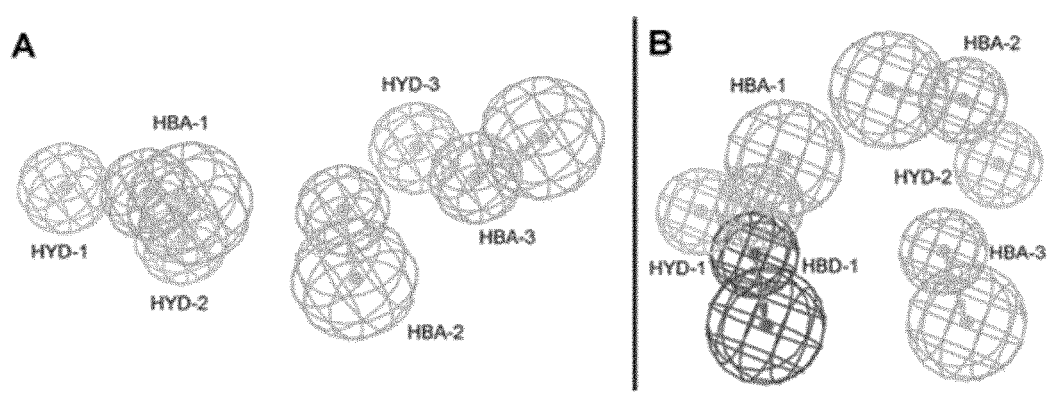

(51) Int. Cl.

| | | |
|---|---|---|
| *A61K 9/127* | (2006.01) | |
| *A61K 45/06* | (2006.01) | |
| *A61K 31/352* | (2006.01) | |
| *A61K 31/121* | (2006.01) | |
| *A61K 31/343* | (2006.01) | |
| *A61K 31/35* | (2006.01) | |

(52) U.S. Cl.
CPC .......... *A61K 31/121* (2013.01); *A61K 31/343* (2013.01); *A61K 31/35* (2013.01); *A61K 31/352* (2013.01); *A61K 45/06* (2013.01)

(58) Field of Classification Search
USPC ........................................................ 549/401
See application file for complete search history.

(56) References Cited

U.S. PATENT DOCUMENTS

| | | | | |
|---|---|---|---|---|
| 2006/0135445 | A1* | 6/2006 | Yamazaki | A61K 31/121 514/27 |
| 2009/0054517 | A1* | 2/2009 | Lubahn | A61K 31/05 514/456 |
| 2009/0203713 | A1 | 8/2009 | Beachy et al. | |
| 2012/0252870 | A1 | 10/2012 | Wei | |
| 2012/0283313 | A1 | 11/2012 | Bergan et al. | |

OTHER PUBLICATIONS

Lee; Bioorganic & Medicinal Chemistry Letters 20 (2010) 6277-6281.*
Slusarz; Cancer Res 2010, 70, 3382-3390.*
Mazumdar; Cancer Res 2011, 71, 5904-5914.*
Sahebjam; The Oncologist 2012, 17, 1090-1099.*
Varnat; EMBO Mol Med 2009, 1, 338-351.*
Yoshimoto; PLOS One 2012, 7, e45332, 1-12.*
Kawaii; Anticancer Research 2012, 32, 5239-5244.*
Alarif; European Journal of Medicinal Chemistry 2013, 66, 204-210.*
Ninomiya; J Nat Med 2013, 67, 460-467.*
Lipinski; Toxicol In Vitro. Aug. 2010 ; 24(5): 1404-1409. doi:10.1016/j.tiv.2010.04.011.*
Arai; Mol. BioSyst., 2013, 9, 1012-1018. DOI: 10.1039/c3mb25567k.*
Rifai; Bioorganic & Medicinal Chemistry Letters 21 (2011) 718-722. doi:10.1016/j.bmcl.2010.11.126.*
Infante; The EMBO Journal (2015) 34: 200-217. DOI 10.15252/embj.201489213.*
Zheng et al., "Synthesis and cytotoxic activity of genistein derivatives", Medical Chemistry Research, 2010, vol. 19, No. 9, pp. 1296-1306.
Hyun et al., "Isoflavones inhibit the clonogenicity of human colon cancer cells", Bioorganic & Medicinal Chemistry Letters, 2012, vol. 22, No. 8, pp. 2664-2669.
Donnelly et al., "Organolead-mediated Arylation of Allyl β-Ketoesters: A Selective Synthesis of Isoflavanones and Isoflavones". J. Chem Soc. Perkin Trans., 1993, No. 15 pp. 1729-1735.
Dhar et al., Database Abstract "Synthetic experiments in the benzopyrone", Journal of Scientific & Industrial Research, 1967, pp. 1-3.
Zemplen et al., Database Abstract "C. Determination of the structure of sophoricoside an iso flavone glycoside of Sophora japonica", Berichte Der Deutschen Chemischen Gesellschaft (Abteilung) B: Abhandlungen, 1943, pp. 1-2.
Biegasiewicz et al., "An efficient synthesis of daidzein, dimethyldaidzein, and isoformononetin", Tettrahedron Letters, 2010, vol. 51, No. 33, pp. 4408-4410.
Delle Monache et al., Database Abstract "3-Aryl-4-methoxycoumarins and isoflavones from Derris glabrescens", Gazette Chimica Italiana, 1998, pp. 1.
Atwood et al., "Hedgehog pathway inhibition and the race against tumor evaluation", The Journal of Cell Biology 2012, vol. 199, pp. 193-197.
International Search Report and Written Opinion for International Application No. PCT/EP2014/063449. (Sep. 1, 2014) (20 Pages).
Chatei et al., "Hedgehog signaling pathway is inactive in colorectal cancer cell lines", Int. J. Cancer, 2007, vol. 121, pp. 2622-2627.

* cited by examiner

A

B

MULTITARGET HEDGEHOG PATHWAY INHIBITORS AND USES THEREOF

CROSS-REFERENCE TO RELATED APPLICATIONS

This application is a 371 of PCT/EP2014/063449, filed Jun. 25, 2014, which claims the benefit of Italian Patent Application No. RM2013A000366, filed Jun. 25, 2013.

FIELD OF THE INVENTION

The present invention concerns compounds that selectively inhibit the activity of the Hedgehog (Hh) pathway, their preparation and uses thereof. Compounds of the present invention are useful in treating Hh-dependent tumors, such as medulloblastoma (MB), and many other cancers.

BACKGROUND OF THE INVENTION

The Hh pathway activation requires the binding of Hh ligands (i.e. Shh, Ihh and Dhh) to the 12-pass membrane receptor Patched (PTCH), plus additional co-receptors. This interaction relieves the inhibitory activity of PTCH on the transducer SMO, a receptor with 7-pass transmembrane domains. In turn, SMO triggers downstream transcription factors belonging to the Gli family (Gli1, Gli2 and Gli3), which act on a set of target genes promoting cell proliferation and reducing cell differentiation. These target genes include Gli1 itself, thus auto-reinforcing the signaling strength and representing a sensitive read out of the pathway.

Hh signaling plays a crucial role in tissues development and proliferation (Ruiz i Altaba, et al. 2002; Ingham and Placzek 2006). A paradigmatic Hh-target organ is cerebellum, where Hh, secreted by Purkinje cells, keeps cerebellar granule cell progenitors (GCPs) proliferating, whereas its termination allows GCPs to exit the cell cycle and differentiate (Dahmane and Ruiz i Altaba 1999; Wallace 1999; Wechsler-Reya and Scott 1999).

Hh pathway is also critical for the maintenance and self-renewal of neural stem cells (NSCs) and for tumorigenesis. More specifically, Hh signaling sustains embryonic and postnatal NSCs of forebrain subventricular zone and hippocampus (Lai, et al. 2003; Machold, et al. 2003; Palma and Ruiz i Altaba 2004; Ahn and Joyner 2005; Palma, et al. 2005), as well as cerebellar NSCs and glioma stem cells (SCs) overexpressing a stemness gene signature (e.g. Nanog, Oct4, Sox2, CD133) (Clement, et al. 2007, Stecca and Ruiz i Altaba 2009).

Constitutive activation of this pathway is responsible for several malignancies, including MB, the most frequent childhood brain tumor (Ruiz i Altaba, et al. 2002). MB belongs to the group of embryonal neuroepithelial tumors and occurs in the cerebellum. This definition emphasizes the peculiar nature of this neoplasm, which is strictly related to the pediatric age; it has an exclusive origin in the only structure of the central nervous system (CNS) that continues its morphogenesis during postnatal life, and it takes origin from stem cells or cerebellar primitive precursor cells.

Aberrant Hh signaling occurs in MB as a consequence of genetic or epigenetic changes affecting several components of the pathway (Di Marcotullio, et al. 2006; Teglund and Toftgard 2010). Failure to switch off growth promoted by Hh signals during GCPs development is a primary event in MB development. Indeed, germline and somatic gain-of-function (SMO) or loss-of-function (PTCH and SUFU) mutations in components of the Hh signaling, all leading to activation of ligand-independent signals, are observed in human MB (Ellison et al., 2002; Taylor, et al. 2002). Further, mouse models in which heterozygous deletion of PTCH or activatory mutations of SMO genes result in tumor development confirm the idea that uncontrolled activation of the Hh pathway sustains the development of MB (Goodrich, et al. 1997; Hallahan, et al. 2004).

The management of this type of tumor requires aggressive treatments consisting in surgical resection followed by radiation and standard chemotherapy. Unfortunately, current therapies have serious adverse effects and patients with recurrent disease after primary therapy have a particularly poor prognosis. This is probably due to the presence in tumor mass of cancer stem cells that exhibit an increased resistance to conventional tumor treatment. In the last few years, several publications have suggested the Hh pathway as a 'druggable' therapeutic target in cancer, since its critical role in the maintenance of cancer stem cells in tumors. Experimental use of Hh antagonists has indicated that Hh suppression has an inhibitory effect on tumor growth in vivo and a number of Hh pathway inhibitors have been developed and patented (for a review see (Tremblay, et al. 2009). Most of these compounds act on and inhibit SMO activity. The natural teratogenic compound cyclopamine, the first identified SMO inhibitor, slows down the growth of tumors in various animal models, thus validating SMO as therapeutic target in the treatment of Hh-related diseases. Recently, several highly potent SMO antagonists have been described. Among these, vismodegib (GDC-0449) has been intensively tested and has demonstrated good inhibitory activity on the Hh pathway. This agent has been approved from FDA on January 2012 for the treatment of adults with metastatic basal cell carcinoma (BCC) or with locally advanced BCC and is currently undergoing phase II clinical trials for the treatment of ovarian, colorectal cancer and MB (for a review see De Smaele, et al. 2010). However, recent studies have described a potential mechanism of escape from vismodegib activity. In fact, it has been reported that after an initial response a patient with MB showed tumor regrowth within 3 months due to a SMO mutation (D473H) able to confer resistance to vismodegib. A mutation altering the corresponding murine residue (D477G) also arose in a vismodegib-resistant mouse model of MB (Yauch, et al. 2009; Dijkgraaf, et al. 2011). The development of resistance was also observed in mice exhibiting MB treated by SMO antagonist NVP-LDE225, which has also been progressed into clinical trials (Buonamici, et al. 2010). These findings demonstrate that acquired mutations in SMO can serve as a mechanism of drug resistance in human cancer and, in particular, underscore the need to identify new effective SMO inhibitors able to counteract tumor growth.

Further, SMO-independent Hh pathway activation, such as mutation in or loss of heterozygosity of SuFu gene (Suppressor of Fused homolog; SuFu is a physiological inhibitor of Gli1) (Taylor, et al. 2002), Gli gene amplification (Kinzler, et al. 1987) and Gli1 translocation (Dahlen, et al. 2004), has also been reported in MB and other tumor such as esophageal adenocarcinoma. This raises the need to identify novel drugs able to block Hh pathway downstream of SMO, such as targeting Gli1, the most powerful effector of the pathway.

SUMMARY OF THE INVENTION

In the present invention it was surprisingly found that compounds having a general formula I

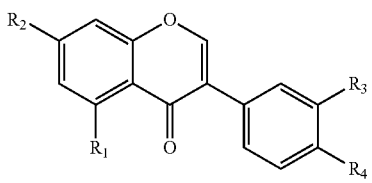

I selectively inhibit the activity of Hedgehog (Hh) pathway. One example of such compounds is Glabrescione B, an isoflavone having the chemical formula (a) which is found naturally in the seeds of *Derris Glabrescens* (Leguminosae).

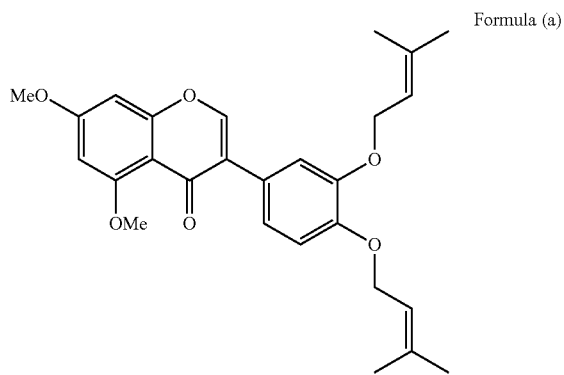 [SMILES: COc1cc(OC)c2c(=O)c(-c3ccc(OCC=C(C)C)c(OCC=C(C)C)c3)coc2c1]

Formula (a)

Its formula comprises the 5,7-dimethoxyisoflavone nucleus and can be obtained according to Delle Monache, Valera et al. 1977.

Figure 4:
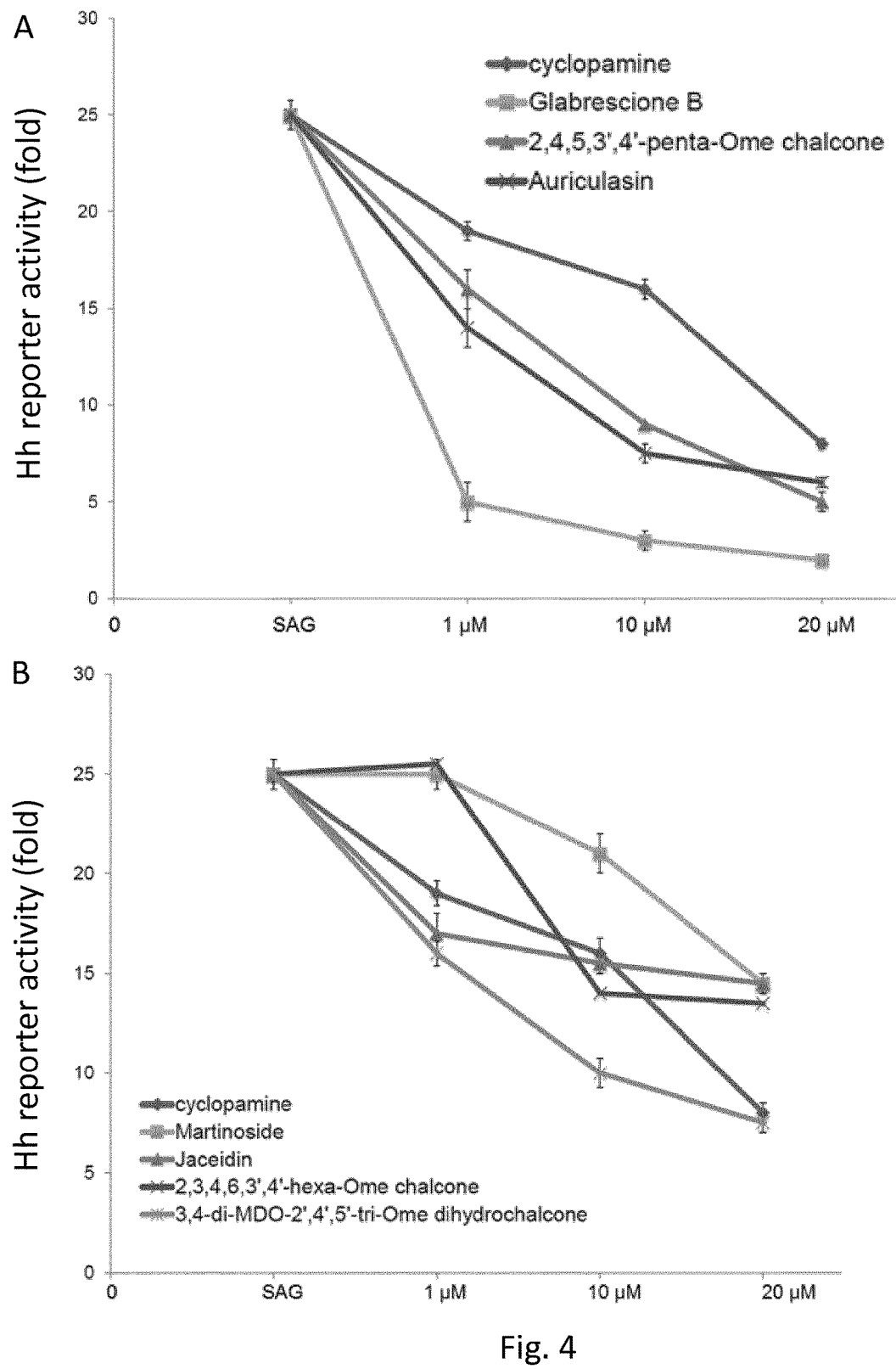

Authors used pharmacophore models for prioritizing possible SMO antagonists among a unique library of more than 800 natural compounds. Two different kinds of pharmacophores were generated, based on the different combination of pharmacophoric features, namely Type1 (FIG. 1A) and Type2 (FIG. 1B). The pharmacophore alignment of Glabrescione B to the representative Type1 pharmacophore model is showed in FIG. 2. After pharmacophore screening, 16 molecules were selected and tested in vitro. Among them, 7 molecules (Glabrescione B, 2,4,5,3',4'-penta-OMe Chalcone, Jaceidin, Auriculasin, 3,4-di-MDO-2',4',5'-tri-OMe dihydrochalcone, 2,3,4,6,3',4'-hexa-OMe Chalcone and Martinoside) turned out to inhibit the Hh pathway in a luciferase assay where the gene reporter was Gli1 and the pathway was activated by the SAG molecule, a potent SMO agonist. The effect of these molecule was comparable up to stronger than that of cyclopamine, the reference natural compound inhibitor of the Hh pathway (FIG. 4). Glabrescione B was the most potent lead identified in vitro. Notably, compounds not active in vitro have an average molecular weight significantly higher than the active compounds, probably meaning that the SMO ligand binding site is not large enough to accommodate these molecules. Contrarily, when the 3D structure of the target receptor is known from X-ray crystallography or NMR spectroscopy, structure-based methods for ligand design may be preferred. Authors used molecular dynamics (MD) to relax the crystallographic structure of the Gli1 zinc finger domain (Gli1-ZF) in complex with DNA and molecular docking to screen the in house library of natural products towards the MD-relaxed Gli1-ZF structure. Notably Glabrescione B, which was already found to antagonize the SMO receptor, was found within the top-ranking positions of the docking-based virtual screening and was therefore tested as Gli1 antagonist in vitro. Results showed that Glabrescione B is a potent Hh inhibitor acting on both SMO and Gli1 targets.

Since Glabrescione B was the most potent Hh inhibitor identified by the screening, a number of Glabrescione B analogues (namely NT8, NT9, NT10, NT11, NT12, NT13, NT14 and NT15) were synthesized and preliminarily tested in vitro to improve inhibitory potency against the Hh pathway and to afford Structure-Activity Relationships (SAR) for the congeneric series (see examples 8 and 9). Evaluation of the Hh inhibitory activity of these molecules was conducted at 5 µM in vitro on Shh Light II cells (see example 2). Preliminary results showed that some of these molecules were at least active as Glabrescione B, with NT8 and NT9 being more potent than Glabrescione B.

The direct interaction of Glabrescione B with the SMO receptor was confirmed by a displacement assay with Bodipy-cyclopamine (see example n.1) while the direct binding of Glabrescione B to Gli1 was monitored via NMR spectroscopy (see example n. 14).

The present invention also provides methods of synthesizing the compounds, in particular Glabrescione B and its derivatives (NT8, NT9, NT10, NT11, NT12, NT13, NT14 and NT15), through a process consisting of subsequent synthetic transformations. In the field of therapeutically treatment of MB some active principles of the class of isoflavones are already known, the most widespread among them being genistein. Studies and experimentations carried out to that aim within the present invention resulted in the total synthesis of Glabrescione B and its derivatives. Chemical characterization of the mentioned compound of the present invention is given further in the example n.7, and the pharmacological data proving the high anticancer activity of said compounds are reported. The isoflavone Glabrescione B was efficiently synthesized from 2,4,6-trimetoxyacetophenone by a six-steps procedure involving the formation of an enamino ketone, followed by ring closure and a Suzuki coupling reaction using the Pd EnCat®40 catalyst.

NT compounds, which have different substituents on ring B, were efficiently synthesized through a different method, starting from a Friedel-Craft acylacion between 3,5-dimethoxyphenol and 3,4-dihydroxyphenylacetic acid by a three-steps procedure. The Glabrescione B was also synthesized by this pathway providing an increased yield and reduced number of steps. Chemical characterization of the mentioned compounds of the present invention is given further in the example n.8 and n.9.

The compounds of the present invention are surprisingly useful in treating Hh-dependent tumors, such as medulloblastoma MB, an aggressive pediatric tumor arising from aberrant development of the cerebellum, and many others cancers including basal cell carcinomas (BCCs) pancreatic, prostate, and small cell lung cancer that account for up to 25% of all human cancer deaths (Epstein, 2008)

In particular, the compounds of the present invention are shown to bind to SMO receptor and/or to target the Gli1 protein, being therefore inhibitors of the Hedgehog pathway. The compounds of formula (I) of the present invention are highly useful in cancer therapy, in the treatment of MB and other tumors that use the Hh signal transduction pathway for proliferation and prevention of apoptosis.

It is an embodiment of the present invention a compound having the general formula I:

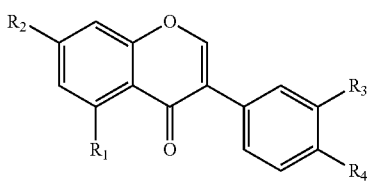

wherein $R_1$ is hydrogen; halogen; acyclic branched or straight, saturated or unsaturated aliphatic chain having from 1 to 10 carbon atoms; acyclic branched or straight, saturated or unsaturated aliphatic chain containing one, two, or three heteroatoms selected from nitrogen, oxygen, and sulphur and having from one to ten carbon atoms; $OR_A$; $C(=O)R_A$; $C(=O)OR_A$; $OC(=O)R_A$; $OSO_3$; $OSO_2R_A$; $SO_2R_A$; $SO_3R_A$; $N(R_A)_2$; $NHC(=O)R_A$; $C(=O)N(R_A)_2$; or $C(R_A)_3$; wherein each occurrence of $R_A$ is independently hydrogen, branched or straight, saturated or unsaturated aliphatic chain having from 1 to 10 carbon atoms or branched or straight, saturated or unsaturated aliphatic chain containing one, two, or three heteroatoms selected from nitrogen, oxygen, and sulphur and having from one to ten carbon atoms, acyl, $C_1$-$C_{10}$alkoxy, $C_1$-$C_{10}$alkylthio, amino, $C_1$-$C_{10}$alkylamino, $C_1$-$C_{10}$dialkylamino;

$R_2$ is hydrogen; halogen; acyclic branched or straight, saturated or unsaturated aliphatic chain having from 1 to 10 carbon atoms; acyclic branched or straight, saturated or unsaturated aliphatic chain containing one, two, or three heteroatoms selected from nitrogen, oxygen, and sulphur and having from one to ten carbon atoms; $OR_B$; $C(=O)R_B$; $C(=O)OR_B$; $OC(=O)R_B$; $OSO_3$; $OSO_2R_B$; $SO_2R_B$; $SO_3R_B$; $N(R_B)_2$; $NHC(O)R_B$; $C(=O)N(R_B)_2$; or $C(R_B)_3$; wherein each occurrence of $R_B$ is independently hydrogen, branched or straight, saturated or unsaturated aliphatic chain having from 1 to 10 carbon atoms or branched or straight, saturated or unsaturated aliphatic chain containing one, two, or three heteroatoms selected from nitrogen, oxygen, and sulphur and having from one to ten carbon atoms, acyl, $C_1$-$C_{10}$alkoxy, $C_1$-$C_{10}$alkylthio, amino, $C_1$-$C_{10}$alkylamino, $C_1$-$C_{10}$dialkylamino;

$R_3$ is hydrogen; $OR_C$; $C(=O)R_C$; $C(=O)OR_C$; $OC(=O)R_C$; $N(R_C)_2$; $NHC(=O)R_C$; $C(=O)N(R_C)_2$; $SR_C$; $CH_2R_C$ or $C(R_C)_3$; wherein $R_C$ is independently, methyl, ethyl, propyl, isopropyl, prenyl, geranyl, farnesyl, benzyl; $O(CH_2)$n-phenyl wherein n is 1, 2 or 3, $O(CH=CH)$Phenyl, $O(CH=CH-CH_2)$Phenyl, $O(CH_2-CH=CH)$Phenyl, $O(CH=CH=CH)$Phenyl; wherein the phenyl of $O(CH_2)$n-phenyl, $O(CH=CH)$Phenyl, $O(CH=CH-CH_2)$Phenyl, $O(CH_2-CH=CH)$Phenyl, $O(CH=CH=CH)$Phenyl or the phenyl of the benzyl group may be substituted by halogen, $C_1$-$C_6$ haloalkyl, $C_1$-$C_6$ haloalkoxy, $C_1$-$C_6$ alkyl, $C_1$-$C_6$ alkenyl, $C_1$-$C_6$ alkynyl, $C_1$-$C_6$ alkoxy, $C_1$-$C_6$ alkylthio, amino, $C_1$-$C_6$ alkylamino, $C_1$-$C_6$ dialkylamino;

$R_4$ is hydrogen; $OR_D$; $C(=O)R_D$; $C(=O)OR_D$; $OC(=O)R_D$; $N(R_D)_2$; $NHC(=O)R_D$; $C(=O)N(R_D)_2$; $SR_D$; $CH_2R_D$ or $C(R_D)_3$ wherein $R_D$ is independently, methyl, ethyl, propyl, isopropyl, prenyl, geranyl, farnesyl, benzyl; $O(CH_2)$n-phenyl wherein n is 1, 2 or 3, $O(CH=CH)$Phenyl, $O(CH=CH-CH_2)$Phenyl, $O(CH_2-CH=CH)$Phenyl, $O(CH=CH=CH)$Phenyl; wherein the phenyl of $O(CH_2)$n-phenyl, $O(CH=CH)$Phenyl, $O(CH=CH-CH_2)$Phenyl, $O(CH_2-CH=CH)$Phenyl, $O(CH=CH=CH)$Phenyl or the phenyl of the benzyl group may be substituted by halogen, $C_1$-$C_6$ haloalkyl, $C_1$-$C_6$ haloalkoxy, $C_1$-$C_6$ alkoxy, $C_1$-$C_6$ alkylthio, amino, $C_1$-$C_6$ alkylamino, $C_1$-$C_6$ dialkylamino;

or stereoisomers or a pharmaceutically acceptable salt thereof.

The term "halogen" refers to fluoro, chloro, bromo, or iodo.

As used herein the term "branched or straight, saturated or unsaturated aliphatic chain having from 1 to 10 carbon atoms" refers to a straight or branched $C_1$-$C_{10}$ alkyl, $C_2$-$C_{10}$ alkenyl or $C_2$-$C_{10}$ alkynyl.

The term $C_1$-$C_{10}$ alkyl refers to a straight or branched hydrocarbon chain radical, consisting solely of carbon and hydrogen atoms, having from one to ten carbon atoms. Suitable examples of $C_1$-$C_{10}$ alkyl include methyl, ethyl, n-propyl, isopropyl, butyl, tert-butyl, pentyl, hexyl, heptyl, octyl, nonyl and decyl etc.

The term $C_2$-$C_{10}$ alkenyl refers to a straight or branched unsaturated hydrocarbon chain radical, containing at least one carbon-carbon double bond, consisting solely of carbon and hydrogen atoms, having from two to ten carbon atoms. Suitable examples of $C_2$-$C_{10}$ alkenyl are ethenyl, propenyl, allyl, isobuthenyl, pentenyl, prenyl, esenyl, geranyl, etc.

The term $C_2$-$C_{10}$ alkynyl refers to a straight or branched unsaturated hydrocarbon chain radical, containing at least one carbon-carbon triple bond, consisting solely of carbon and hydrogen atoms, having from two to ten carbon atoms. Suitable examples of $C_2$-$C_{10}$ alkynyl are acetylenyl, ethynyl, propynyl, etc.

Suitable examples of "branched or straight, saturated or unsaturated aliphatic chain containing one, two, or three heteroatoms selected from nitrogen, oxygen, and sulphur and having from one to ten carbon atoms" are ether, tioether, amino, aminoalchol, sulfonamide, $(CH_2)_mNH_2SO_2CH_3$, $(CH_2)_mOH$; $(CH_2)_mOGlucose$, wherein m is a number from 1 to 10; The term "$C_1$-$C_{10}$ alkoxy" refers to a straight or branched O—$C_1$-$C_{10}$ alkyl, where alkyl is as defined herein above. The "$C_1$-$C_{10}$ alkoxy" group is preferably a linear or branched $C_1$-$C_8$ alkoxy group, more preferably a linear or branched $C_1$-$C_6$ alkoxy group, more preferably linear or branched $C_1$-$C_4$ alkoxy group, more preferably $C_1$-$C_2$ alkoxy group.

The term $C_1$-$C_{10}$alkylthio refers to a straight or branched S—$C_1$-$C_{10}$ alkyl, where alkyl is as defined herein above. The "$C_1$-$C_{10}$ alkylthio" group is preferably a linear or branched $C_1$-$C_8$ alkylthio group, more preferably a linear or branched $C_1$-$C_6$ alkylthio group, more preferably linear or branched $C_1$-$C_4$ alkylthio group, more preferably $C_1$-$C_2$ alkylthio group.

The term "$C_1$-$C_{10}$ haloalkyl" refers to a straight or branched hydrocarbon chain radical, which is substituted by one or more halogen atoms and having from one to ten carbon atoms. The "$C_1$-$C_{10}$ haloalkyl" group is preferably a linear or branched $C_1$-$C_8$ haloalkyl group, more preferably linear or branched $C_1$-$C_6$ haloalkyl group, still more preferably linear or branched $C_1$-$C_4$ haloalkyl group, more preferably a $C_1$-$C_2$ haloalkyl group, being in particular $CF_3$.

The term "amino" refers to $NH_2$.

The terms "$C_1$-$C_{10}$alkylamino" and "$C_1$-$C_{10}$dialkylamino" refer to NH—$C_1$-$C_{10}$alkyl and N—($C_1$-$C_{10}$alkyl)$_2$ respectively, where alkyl is as defined herein above.

The term "$C_1$-$C_6$ haloalkoxy" refers to a straight or branched O—$C_1$-$C_6$ haloalkyl, where haloalkyl is as defined herein. The "$C_1$-$C_6$ haloalkoxy" group is preferably a linear or branched $C_1$-$C_4$ haloalkoxy group, more preferably a $C_1$-$C_2$ haloalkoxy group, being in particular $OCF_3$, $OCHF_2$ or $OCH_2F$.

As used herein the term "acyl" refers to $C(O)R_E$ wherein $R_E$ is $C_1$-$C_6$alkyl, where alkyl is as defined herein above.

In a preferred embodiment of the invention the compound has the general formula I wherein $R_1$ is $OR_A$ and $R_A$ is $CH_3$.

In another preferred embodiment of the invention the compound has the general formula I wherein $R_2$ is $OR_B$ and $R_B$ is $CH_3$.

In another preferred embodiment of the invention $R_1$ is $OR_A$ and $R_A$ is $CH_3$ and $R_2$ is $OR_B$ and $R_B$ is $CH_3$.

In preferred embodiment of the invention the compound has the general formula I wherein $R_3$ is $OR_C$ and $R_C$ is methyl, ethyl, propyl, isopropyl, prenyl, geranyl, farnesyl or benzyl, wherein the phenyl of the benzyl group may be substituted by halogen, $C_1$-$C_6$ haloalkyl, $C_1$-$C_6$ haloalkoxy, $C_1$-$C_6$ alkoxy, $C_1$-$C_6$ alkylthio, amino, $C_1$-$C_6$ alkylamino, $C_1$-$C_6$ dialkylamino.

In another preferred embodiment of the invention $R_1$ is $OR_A$ and $R_A$ is $CH_3$ and $R_3$ is $OR_C$ and $R_C$ is methyl, ethyl, propyl, isopropyl, prenyl, geranyl, farnesyl or benzyl, wherein the phenyl of the benzyl group may be substituted by halogen, $C_1$-$C_6$ haloalkyl, $C_1$-$C_6$ haloalkoxy, $C_1$-$C_6$ alkoxy, $C_1$-$C_6$ alkylthio, amino, $C_1$-$C_6$ alkylamino, $C_1$-$C_6$ dialkylamino.

In another preferred embodiment of the invention $R_2$ is $OR_B$ and $R_B$ is $CH_3$ and $R_3$ is $OR_C$ and $R_C$ is methyl, ethyl, propyl, isopropyl, prenyl, geranyl, farnesyl or benzyl, wherein the phenyl of the benzyl group may be substituted by halogen, $C_1$-$C_6$ haloalkyl, $C_1$-$C_6$ haloalkoxy, $C_1$-$C_6$ alkoxy, $C_1$-$C_6$ alkylthio, amino, $C_1$-$C_6$ alkylamino, $C_1$-$C_6$ dialkylamino.

In another preferred embodiment of the invention $R_1$ is $OR_A$ and $R_A$ is $CH_3$ and $R_2$ is $OR_B$ and $R_B$ is $CH_3$ and $R_3$ is $OR_C$ and $R_C$ is methyl, ethyl, propyl, isopropyl, prenyl, geranyl, farnesyl or benzyl, wherein the phenyl of the benzyl group may be substituted by halogen, $C_1$-$C_6$ haloalkyl, $C_1$-$C_6$ haloalkoxy, $C_1$-$C_6$ alkoxy, $C_1$-$C_6$ alkylthio, amino, $C_1$-$C_6$ alkylamino, $C_1$-$C_6$ dialkylamino.

In another preferred embodiment of the invention $R_4$ is $OR_D$ and $R_D$ is methyl, ethyl, propyl, isopropyl, prenyl, geranyl, farnesyl or benzyl, wherein the phenyl of the benzyl group may be substituted by halogen, $C_1$-$C_6$ haloalkyl, $C_1$-$C_6$ haloalkoxy, $C_1$-$C_6$ alkoxy, $C_1$-$C_6$ alkylthio, amino, $C_1$-$C_6$ alkylamino, $C_1$-$C_6$ dialkylamino.

In another preferred embodiment of the invention $R_1$ is $OR_A$ and $R_A$ is $CH_3$ and $R_4$ is $OR_D$ and $R_D$ is methyl, ethyl, propyl, isopropyl, prenyl, geranyl, farnesyl or benzyl, wherein the phenyl of the benzyl group may be substituted by halogen, $C_1$-$C_6$ haloalkyl, $C_1$-$C_6$ haloalkoxy, $C_1$-$C_6$ alkoxy, $C_1$-$C_6$ alkylthio, amino, $C_1$-$C_6$ alkylamino, $C_1$-$C_6$ dialkylamino.

In another preferred embodiment of the invention $R_2$ is $OR_B$ and $R_B$ is $CH_3$ and $R_4$ is $OR_D$ and $R_D$ is methyl, ethyl, propyl, isopropyl, prenyl, geranyl, farnesyl or benzyl, wherein the phenyl of the benzyl group may be substituted by halogen, $C_1$-$C_6$ haloalkyl, $C_1$-$C_6$ haloalkoxy, $C_1$-$C_6$ alkoxy, $C_1$-$C_6$ alkylthio, amino, $C_1$-$C_6$ alkylamino, $C_1$-$C_6$ dialkylamino.

In still another preferred embodiment of the invention $R_1$ is $OR_A$ and $R_A$ is $CH_3$ and $R_2$ is $OR_B$ and $R_B$ is $CH_3$, $R_3$ is $OR_C$ and $R_C$ is methyl, ethyl, propyl, isopropyl, prenyl, geranyl, farnesyl or benzyl, wherein the phenyl of the benzyl group may be substituted by halogen, $C_1$-$C_6$ haloalkyl, $C_1$-$C_6$ haloalkoxy, $C_1$-$C_6$ alkoxy, $C_1$-$C_6$ alkylthio, amino, $C_1$-$C_6$ alkylamino, $C_1$-$C_6$ dialkylamino and $R_4$ is $OR_D$ and $R_D$ is methyl, ethyl, propyl, isopropyl, prenyl, geranyl, farnesyl or benzyl, wherein the phenyl of the benzyl group may be substituted by halogen, $C_1$-$C_6$ haloalkyl, $C_1$-$C_6$ haloalkoxy, $C_1$-$C_6$ alkoxy, $C_1$-$C_6$ alkylthio, amino, $C_1$-$C_6$ alkylamino, $C_1$-$C_6$ dialkylamino.

In a preferred embodiment the compound of formula (I) is:

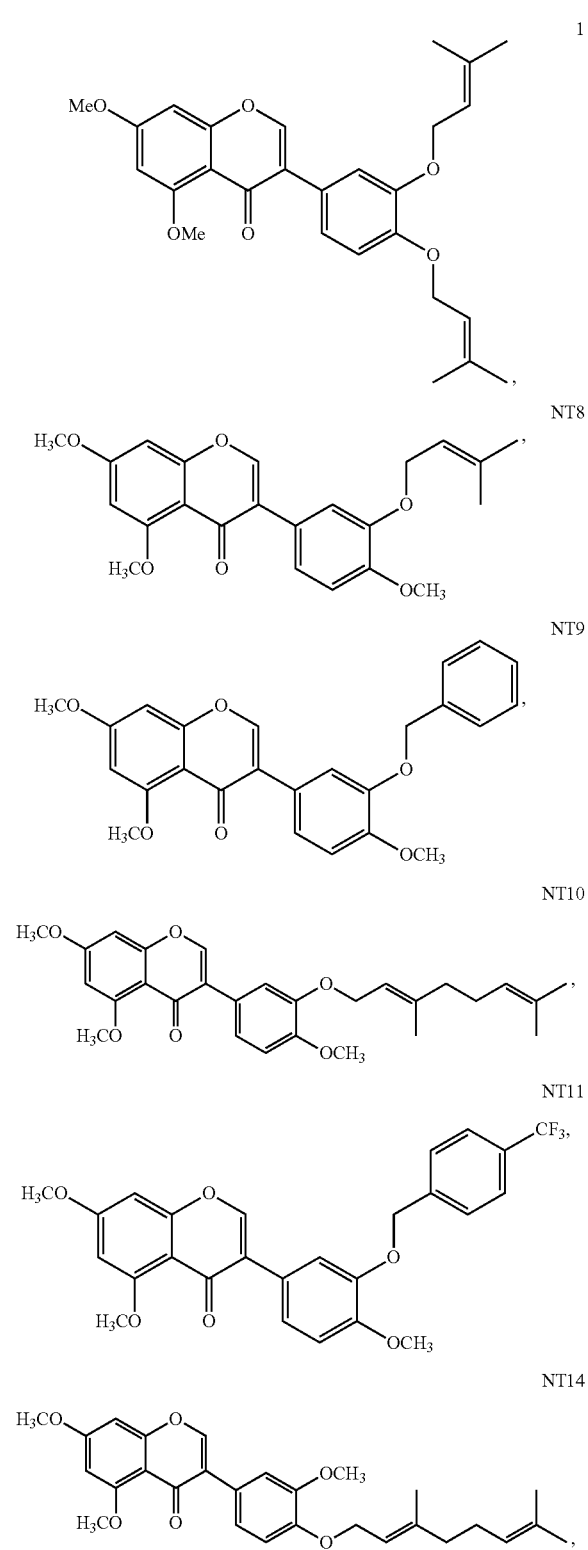

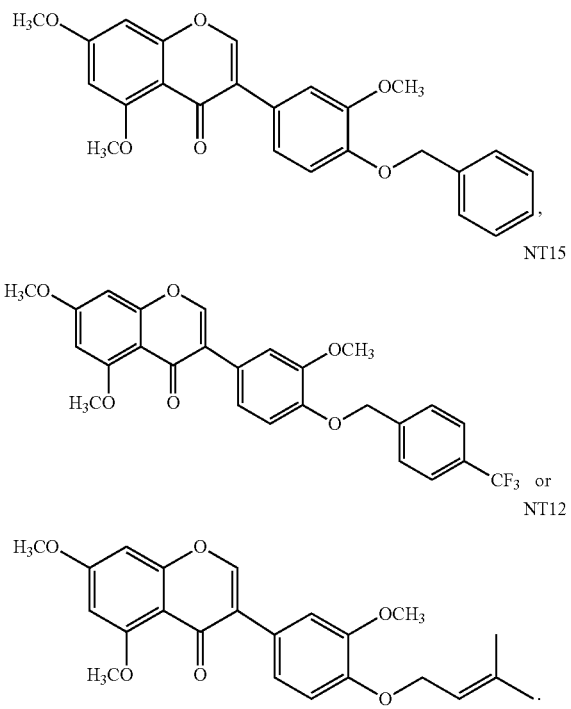

In a further embodiment the compounds of the invention are for use as Hedgehog (Hh) pathway inhibitor.

In a further embodiment the compounds of the invention are for use as a ligand of the serpentine Smoothened (SMO)/Hh receptor and/or of Gli1.

In a further embodiment the compounds of the invention are for use as medicament.

In still a further embodiment the compounds of the invention are for use in the treatment of a Hedgehog (Hh)-dependent pathology, more preferably the Hh-dependent pathology is a tumor. Still preferably the Hh-dependent pathology is resistant to a SMO inhibitor, preferably vismodegib or NVP-LDE225.

Preferably the tumor is selected from the group consisting of: medulloblastoma (MB), esophageal adenocarcinoma, basal cell carcinomas (BCCs), pancreatic, prostate, and small cell lung cancer. More preferably the tumor is present in a pediatric subject.

"Pharmaceutically acceptable salt" comprise a conventional non-toxic salt obtained by salification of a compound of formula (I) with inorganic acids (e.g. hydrochloric, hydrobromic, sulphuric or phosphoric acids), or with organic acids (e.g. acetic, propionic, succinic, benzoic, sulfanilic, 2-acetoxy-benzoic, cinnamic, mandelic, salicylic, glycolic, lactic, oxalic, malic, maleic, malonic, fumaric, tartaric, citric, p-toluenesulfonic, methanesulfonic, ethanesulfonic, or naphthalensulfonic acids).

In addition pharmaceutically acceptable base addition salts can be formed with a suitable inorganic or organic base such as triethylamine, ethanolamine, triethanolamine, choline, arginine, lysine or histidine. Other suitable pharmaceutically acceptable salts include pharmaceutically acceptable alkali-metal or alkaline-earth-metal salts such as sodium, potassium, calcium or magnesium salts; in particular pharmaceutically acceptable salts of one or more carboxylic acid moieties that may be present in the compound of formula (I).

For reviews on suitable pharmaceutical salts see Berge S. M. et al., J. Pharm. Sci. 1977, 66, 1-19; Gould P. L. Int. J. Pharm 1986, 33, 201-217; and Bighley et al. Encyclopedia of Pharmaceutical Technology, Marcel Dekker Inc, New York 1996, Volume 13, page 453-497. Other salts, which are not pharmaceutically acceptable, for example the trifluoroacetate salt, may be useful in the preparation of compounds of this invention and these form a further aspect of the invention. The invention includes within its scope all possible stoichiometric and non-stoichiometric forms of the salts of the compounds of formula (I).

In addition, the compounds of the present invention can exist in unsolvated as well as in solvated forms with pharmaceutically acceptable solvents such as water, ethanol and the like and these forms are also included within the scope of the present invention.

The compounds of formula (I) of the invention have asymmetric carbon atoms and may therefore exist as individual optical isomers, as racemic mixtures or as any other mixture comprising a majority of one of the two optical isomers, which are all to be intended as within the scope of the present invention.

Likewise, it is understood that compounds of the invention may exist in tautomeric forms other than that shown in the formula and these are also included within the scope of the present invention.

The invention also includes all suitable isotopic variations of a compound of formula (I) of the invention. An isotopic variation of a compound of the invention is defined as one in which at least one atom is replaced by an atom having the same atomic number but an atomic mass different from the atomic mass usually found in nature.

Examples of isotopes that can be incorporated into compounds of the invention include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the invention, for example, those in which a radioactive isotope such as $^{3}H$ or $^{14}C$ is incorporated, are useful in drug and/or substrate tissue distribution studies. Tritiated $^{3}H$, and carbon-14 $^{14}C$, isotopes are particularly preferred for their ease of preparation and detectability. Further, substitution with isotopes such as deuterium $^{2}H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the examples hereafter using appropriate isotopic variations of suitable reagents.

It is a further embodiment of the invention a pharmaceutical composition comprising at least one compound of the invention as defined herein above and a carrier and/or suitable excipients and/or diluents. Preferably the carrier is a liposome.

It is a further embodiment of the invention the pharmaceutical composition as defined herein above further comprising at least one therapeutic agent, preferably selected from the group consisting of anticancer drugs, preferably selected within the group including the following drugs: Temozolomide, Bevacizumab, Gemcitabine, leuprolide acetate, goserelin acetate and Etoposide and Cisplatin.

Preferably the pharmaceutical composition of the invention is to be administered by intratumoral injection.

It is a further embodiment of the invention a method for the treatment of a Hedgehog (Hh)-dependent pathology comprising administering in an effective amount the compound of the invention or the pharmaceutical composition of the invention in a subject in need thereof.

The invention also provides pharmaceutical compositions comprising one or more compounds of this invention and one or more pharmaceutically acceptable excipient and/or diluent. The pharmaceutical compositions can be chosen on the basis of the treatment requirements. Such compositions are prepared by blending and are suitably adapted to oral or parenteral administration, and as such can be administered in the form of tablets, capsules, oral preparations, powders, granules, pills, injectable, or infusible liquid solutions, suspensions, suppositories, preparation for inhalation, intratumoral injection.

Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g. polyvinylpyrrolidone and starch derivatives such as sodium glycolate starch), coloring agents, flavoring agents, and wetting agents (for example sodium lauryl sulfate).

The oral solid compositions can be prepared by conventional methods of blending, filling or tableting. The blending operation can be repeated to distribute the active principle throughout compositions containing large quantities of fillers. Such operations are conventional.

Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatin, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavoring or coloring agents. Oral formulations also include conventional slow-release formulations such as enterically coated tablets or granules.

Pharmaceutical preparation for administration by inhalation can be delivered from an insufflator or a nebulizer pressurized pack.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilising by filtration, filling suitable vials and sealing. Advantageously, adjuvants such as local anaesthetics, preservatives and buffering agents can also be dissolved in the vehicle. To increase the stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the invention.

For buccal or sublingual administration the compositions may be tablets, lozenges, pastilles, or gel.

The compounds can be pharmaceutically formulated as suppositories or retention enemas, e.g. containing conventional suppositories bases such as cocoa butter, polyethylene glycol, or other glycerides, for a rectal administration.

Another means of administering the compounds of the invention regards topical treatment. Topical formulations can contain for example ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. Creams, as known to formulation experts, are viscous liquids or semisolid emulsions, and contain an oil phase, an emulsifier and an aqueous phase. The oil phase generally contains petrolatum and an alcohol such as cetyl or stearic alcohol. Formulations suitable for topical administration to the eye also include eye drops, wherein the active ingredient is dissolved or suspended in a suitable carrier, especially an aqueous solvent for the active ingredient.

A further method of administering the compounds of the invention regards transdermal delivery. Typical transdermal formulations comprise conventional aqueous and non-aqueous vectors, such as creams, oils, lotions or pastes or can be in the form of membranes or medicated patches.

A reference for the formulations is the book by Remington ("Remington: The Science and Practice of Pharmacy", Lippincott Williams & Wilkins, 2000).

The compounds of the present invention may be employed alone as a sole therapy or in combination with other therapeutic agents for the treatment of the above-mentioned conditions.

The combination can be administered as separate compositions (simultaneous, sequential) of the individual components of the treatment or as a single dosage form containing both agents. When the compounds of this invention are in combination with others active ingredients, the active ingredients may be separately formulated into single-ingredient preparations of one of the above-described forms and then provided as combined preparations, which are given at the same time or different times, or may be formulated together into a two- or more-ingredient preparation.

Compounds of general formula (I) may be administered to a patient in a total daily dose of, for example, from 0.001 to 1000 mg/kg body weight daily. Dosage unit compositions may contain such amounts of submultiples thereof to make up the daily dose. The determination of optimum dosages for a particular patient is well known to one skilled in the art.

As is common practice, the compositions are normally accompanied by written or printed instructions for use in the treatment in question.

In the present invention a "Hedgehog (Hh) pathway inhibitor" means a small molecule of natural, semi-synthetic or synthetic origin that is able to inhibit the transduction of the Hedgehog signal within the cell, as measured in vitro and/or in vivo. A Hedgehog pathway inhibitor is therefore a small molecule able to bind to the serpentine Smoothened (SMO)/Hh receptor and/or to the zinc-finger transcription factor Gli1 (P08151)

A Hedgehog pathway inhibitor is therefore of medical relevance for the treatment of a Hedgehog (Hh)-dependent pathology, where a Hedgehog (Hh)-dependent pathology is a disease, most often a cancer, whose development and/or progression are due to aberrant activity of the Hedgehog pathway. Aberrant activity means overexpression, mutation, gain-of-function or loss-of-function of Hedgehog pathway proteins, overproduction of the Hedgehog ligands, decreased ubiquitination-mediated degradation or acetylation of the Gli proteins, gene amplification, increased PI3K/mTOR/S6K1 kinase-dependent phosphorylation, (Di Marcotullio et al, 2006, Di Marcotullio et al, 2011, Atwood et al. 2012).

A SMO antagonist or inhibitor is a small molecule of natural, semi-synthetic or synthetic origin that is able to interact with the SMO receptor and to inhibit the function of the SMO receptor in the context of the Hedgehog pathway.

A Gli1 antagonist or inhibitor is a small molecule of natural, semi-synthetic or synthetic origin that is able to inhibit its function and/or to inhibit its binding to DNA. The desired Gli1 antagonist or inhibitor binds directly to Gli1 and competes with nucleic acids for the same binding site on the surface of Gli1. Another class of Gli1 antagonists or inhibitors bind to other receptors or proteins and hamper Gli1 functions by indirect mechanism.

The invention will now be illustrated by non-limiting examples referring to the following figures.

FIG. 1. Representative Type1 (A) and Type2 (B) pharmacophore models used for screening in house library of natural compounds. Pharmacophoric features are showed as spheres. Hydrogen bond acceptor (HBA); hydrophobic (HYD); Hydrogen bond donor (HBD).

Figure 2:
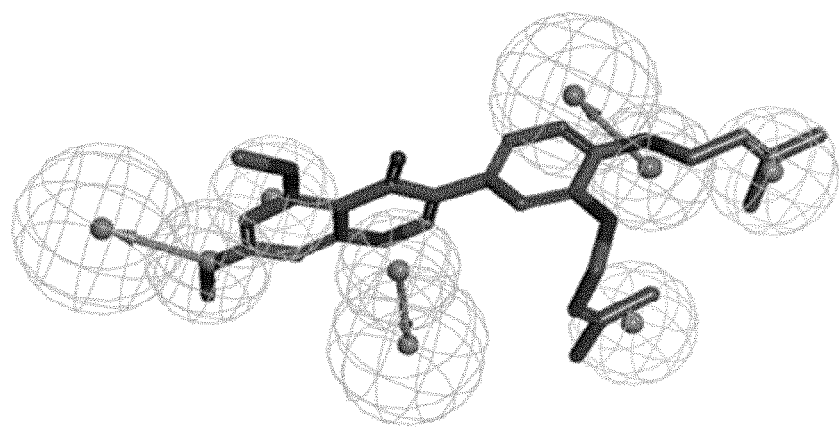

FIG. 2. The best alignment of the most potent compound Glabrescione B toward the representative Type1 pharmacophore. For clarity, non-polar hydrogen atoms were hidden. Heavy atoms are colored as follows: grey=carbon; red=oxygen.

Figure 3:
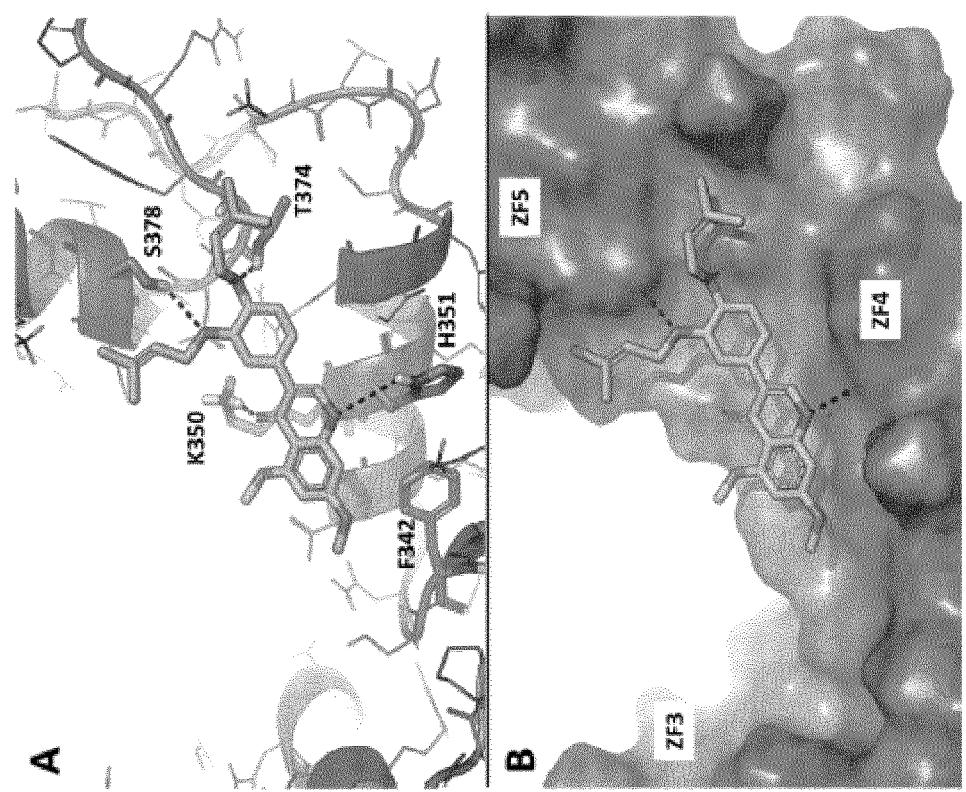

FIG. 3. The predicted binding mode of Glabrescione B (showed as sticks). A: Gli1-ZF (zinc finger) is represented as lines and cartoons. Residues interacting with Glabrescione B are showed as sticks. H-bonds are highlighted by dashed lines. B: Gli1-ZF is showed as transparent surface and Glabrescione B is interacting within ZF4 and ZF5. Zinc fingers 3 and 5 are also labeled. The protein is in the same orientation as in A. T374 is Threonine 374, S378 is Serine 378, K350 is Lysine 350 and F342 is Phenylalanine 342.

FIG. 4. Effect of active natural compounds identified by the pharmacophore screening in a luciferase assay, where the gene reporter was Gli1 and the pathway was activated by the SAG molecule, a potent SMO agonist. Natural compounds were tested at three different concentrations (1, 10 and 20 µM) and their activity was compared to that of cyclopamine, the natural compound reference inhibitor of the Hedgehog pathway, which was tested at the same doses (1, 10 and 20 µM). On both graphs the activity of cyclopamine is reported as reference standard. (A) cyclopamine, 2,4,5,3',4'-penta-Ome chalcone and Auriculasin; (B) cyclopamine, Martinoside, Jaceidin, 2,4,5,3',4'-penta-Ome chalcone, 3,4-di-MDO-2',4',5'-tri-Ome dihydrochalcone.

Figure 5:
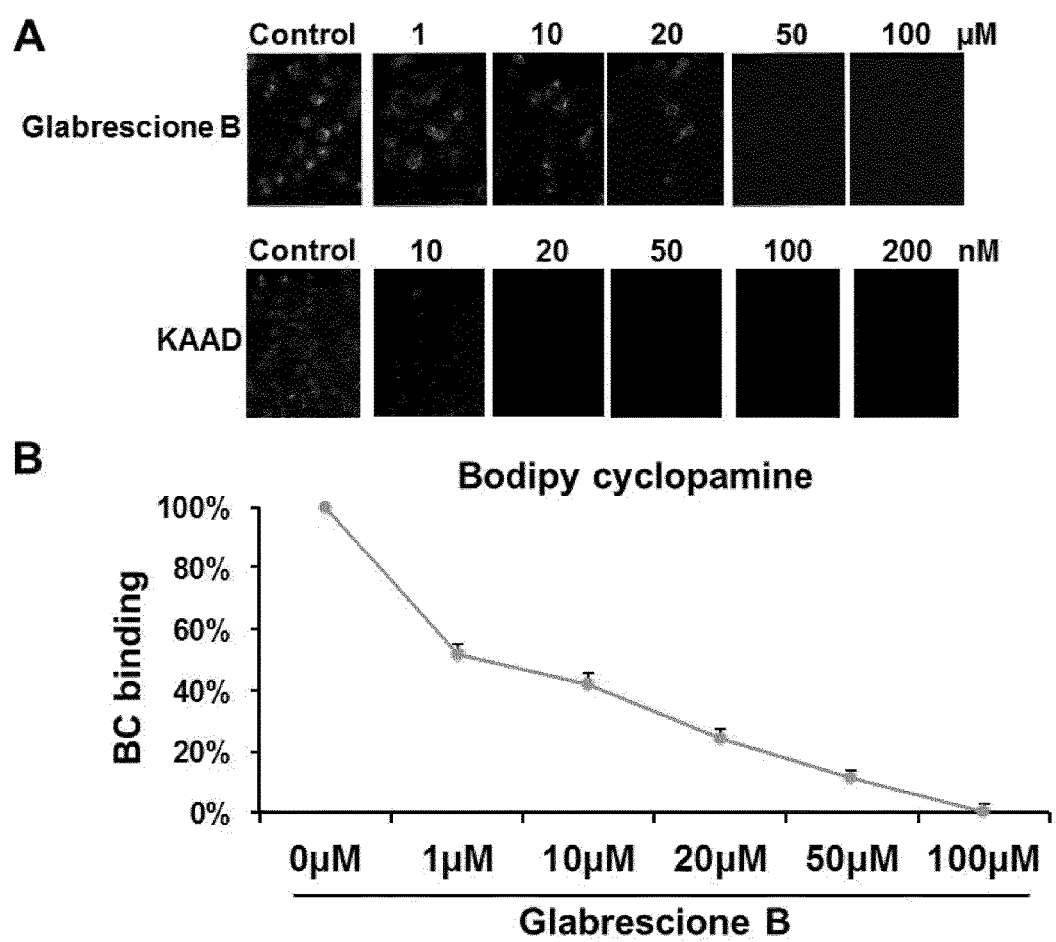

FIG. 5. (A) HEK293 cells were transiently transfected with pcDNA-SMO vector and incubated with Bodipy-cyclopamine (BC 5 nM) alone (control) or in the presence of increasing concentrations of KAAD (Cyclopamine-KAAD, Smoothened antagonist) or increasing concentrations of Glabrescione B, as indicated. Bodipy-cyclopamine binding (BC binding) (green) is visualized using fluorescence microscopy in a representative field. (B) The concentration-response curve for Glabrescione B was obtained by quantification of the Bodipy-cyclopamine fluorescence in three photographs for each coverslip. The values are expressed as a percentage of the fluorescence detected in control HEK293 cells incubated with Bodipy-cyclopamine alone. The data shown are the means of triplicates derived from a representative experiment of three. Error bars indicate SD (standard deviation).

Figure 6:
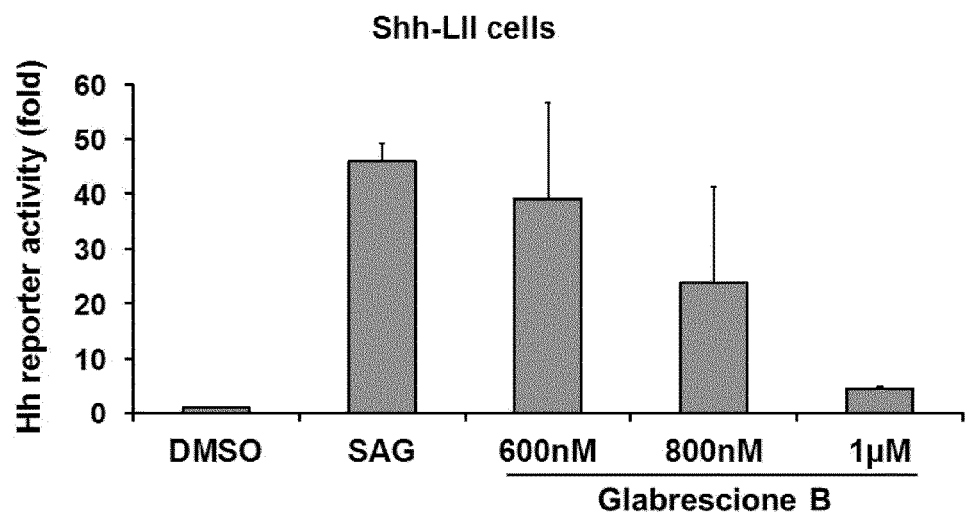

FIG. 6. Dose-response curve of Glabrescione B in SAG (Smoothened Agonist, 200 nM) treated NIH 3T3 Shh-light II (Shh-LII) cells. Treatment time was 48 h and normalization was against *Renilla* luciferase. Shown is the fold increase of Hh reporter activity compared with cells not treated with SAG.

Figure 7:
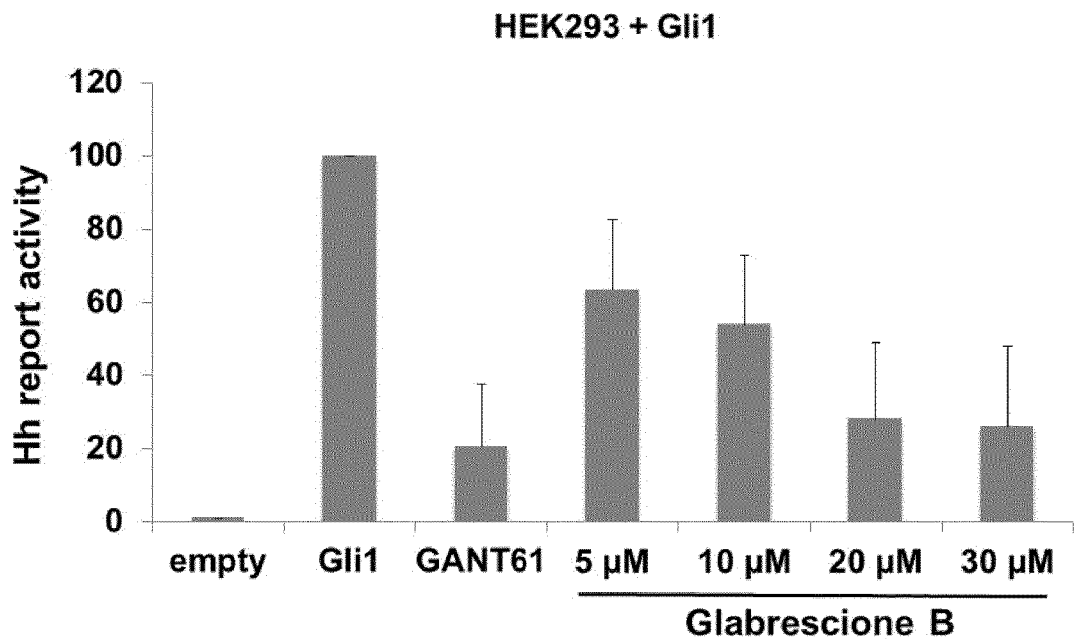

FIG. 7. Inhibition of Gli1-induced transcription in transfected HEK293 cells. HEK293 cells were transfected with 12×GliBS-Luc and pRL-TK *Renilla* (normalization control) plus control (empty vector) or Gli1 vector and treated with Glabrescione B or GANT61 (20 µM) or vehicle only (DMSO, dimethyl sulfoxide 0.5%—Gli1 bar in the graph) for 24 h and luciferase activity tested. Shown is the mean of three independent experiments. Error bars indicate SD.

Figure 8:
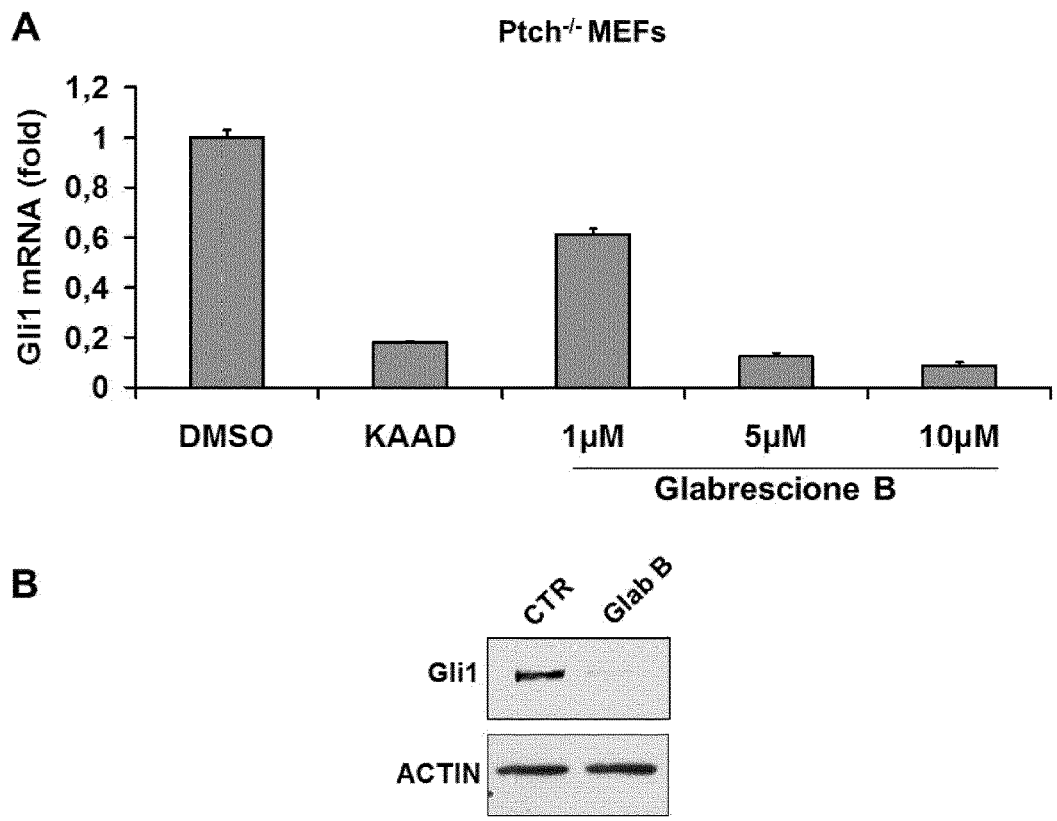

FIG. 8. Confluent MEF-Ptch$^{-/-}$ cells were treated with DMSO (0.5%, vehicle), KAAD (1 µM, as positive control) or different concentrations of Glabrescione B for 48 h. (A) Gli1 mRNA levels were determined by quantitative RT-PCR, normalizing to HPRT (Hypoxanthine-guanine phosphoribosyl transferase) expression. Error bars indicate SD. (B) Western blot analysis shows the decrease of Gli1 protein levels after 48 h of treatment with compound 10 µM.

Figure 9:
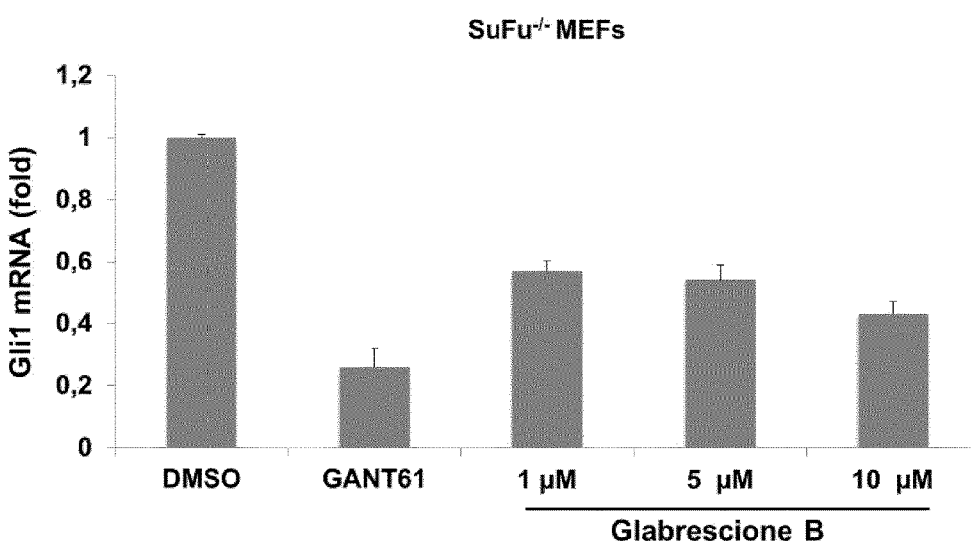

FIG. 9. Confluent MEF-SuFu$^{-/-}$ cells were treated with DMSO (0.5%, vehicle), GANT61 (10 µM, as positive control) or different concentrations of Glabrescione B for 48 h. Gli1 mRNA levels were determined by quantitative RT-PCR, normalizing to HPRT expression. Error bars indicate SD.

Figure 10:
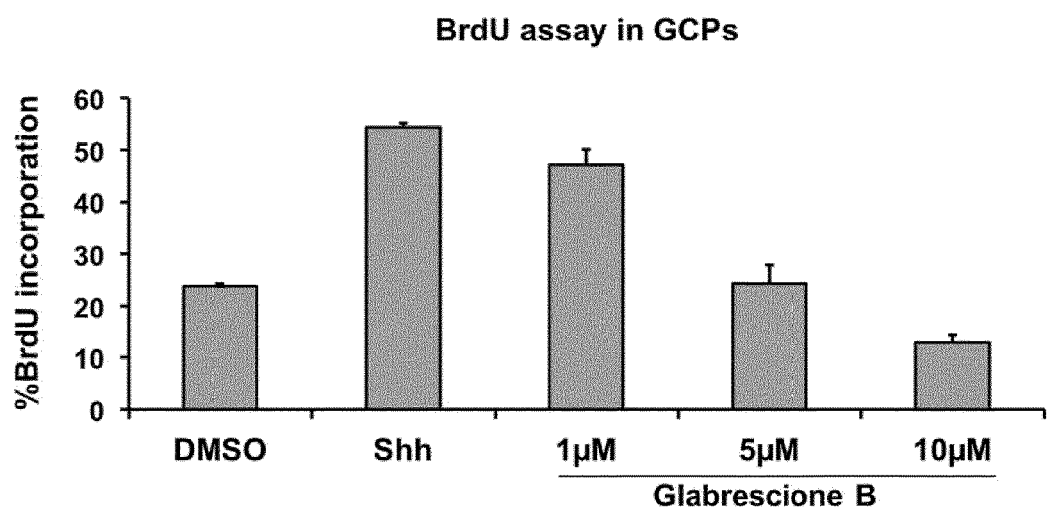

FIG. 10. Cerebellar granule progenitor cells (GCPs) were treated with Shh (Recombinant mouse Sonic Hedgehog, amino-terminal peptide, 3 µg/ml) and with different concentrations of Glabrescione B, as indicated, for 48 h. Inhibition of cell proliferation was measured as percentage of BrdU incorporation in comparison to DMSO (0.5%, vehicle) treated sample.

Figure 11:
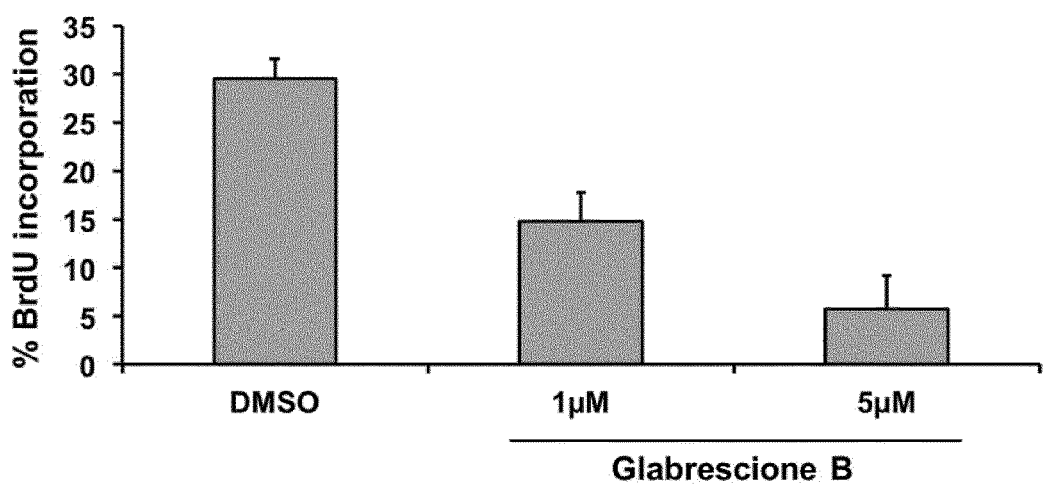
Figure 11:
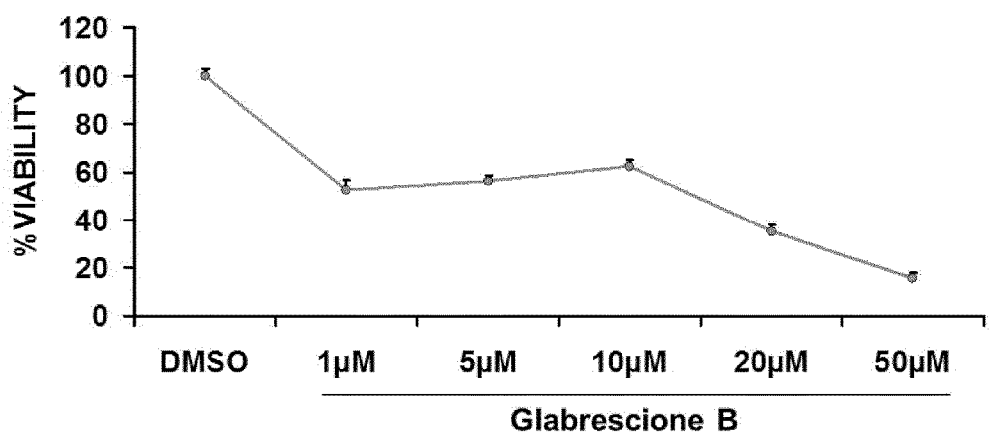

FIG. 11. (A) Human MB D283 cells were treated with different concentrations of Glabrescione B as indicated for 48 h. Inhibition of cell proliferation was measured as percentage of BrdU incorporation in comparison to DMSO (0.5%, vehicle) treated sample. (B) Human MB D283 cells were treated for 48 h with increasing concentrations of Glabrescione B as indicated. After 48 h, CellTiter 96® Aqueous One Solution Reagent was added to each well according to the manufacturer's instructions. After one hour in culture the cell viability (expressed in % viability) was determined by measuring the absorbance at 490 nm comparing treatment with DMSO (0.5%, vehicle) control.

Figure 12:
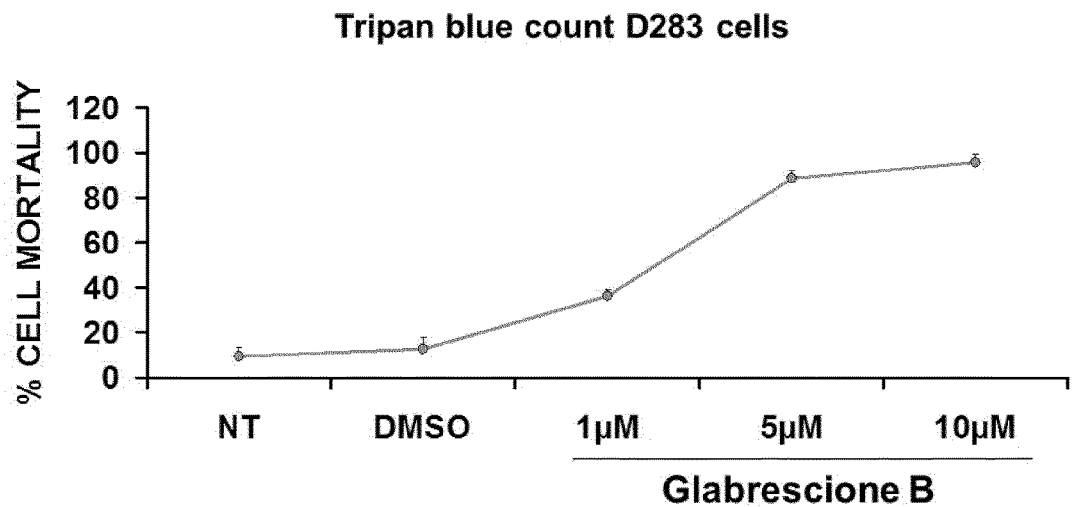

FIG. 12. Human MB D283 cells were treated with the DMSO (0.5%, vehicle) or with different concentrations of Glabrescione B as indicated and compared to an untreated sample (NT). After 48 h a tripan blue count was performed to determine the percentage of cell death.

Figure 13:
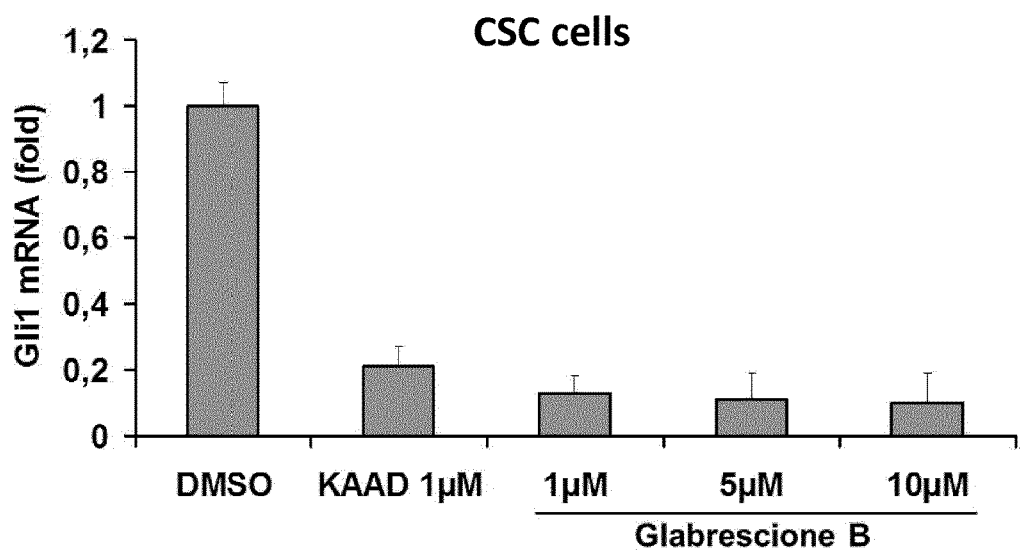

FIG. 13. Cancer stem cells (CSCs) isolated from murine Ptch$^{+/-}$ MB were treated with DMSO (0.5%, vehicle), KAAD (1 µM), used as positive control, or different concentrations of Glabrescione B as indicated for 48 h. Gli1 mRNA levels were determined by quantitative RT-PCR using HPRT as normalizer.

Figure 14:
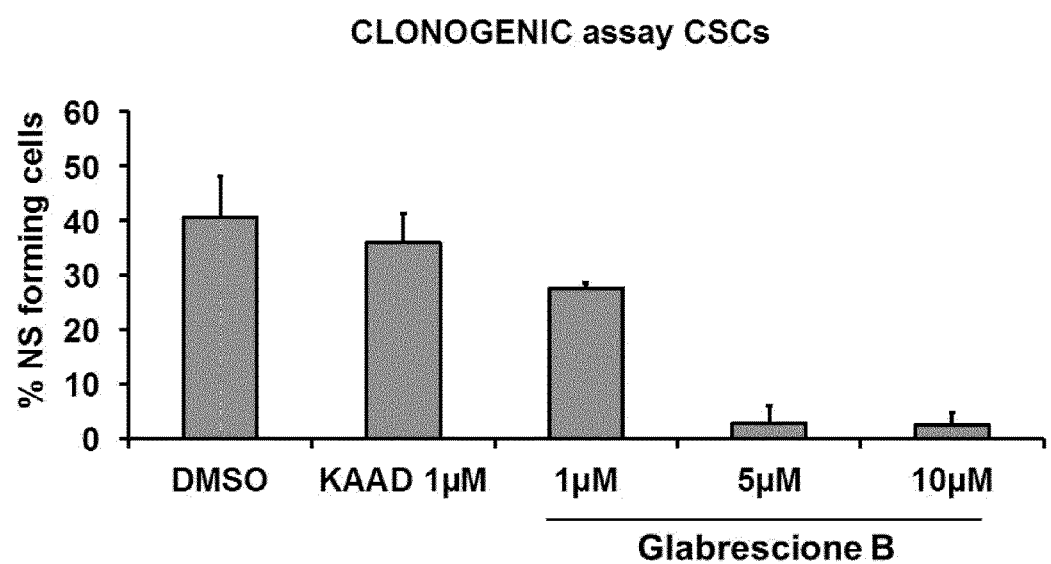

FIG. 14. Suspension of single CSCs isolated from murine Ptch$^{+/-}$ MB were treated with DMSO (0.5%, vehicle), KAAD (1 µM) or different concentrations of Glabrescione B as indicated. After seven days of treatment the number of secondary neurospheres derived from a known number of single cells was counted. The self-renewal CSCs capability is expressed as percentage of neurospheres forming cells.

Figure 15:
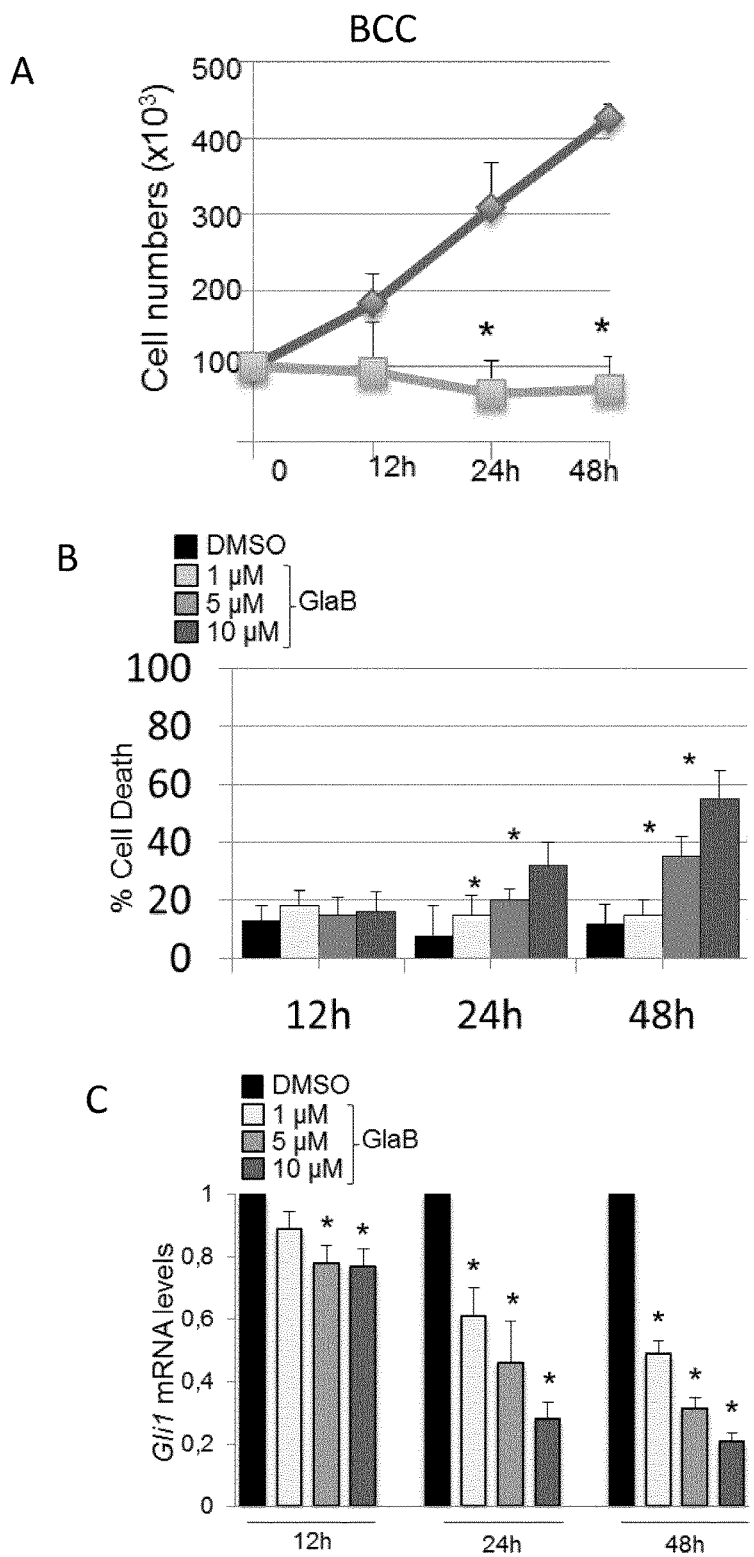

FIG. 15. Inhibition of Gli-dependent BCC tumor cell growth. ASZ001 BCC cells were treated with Glabrescione B (GlaB) 5 μM or DMSO only (A) or with Glabrescione B 1, 5 and 10 μM (GlaB) or DMSO only (B). After the indicated times, a trypan blue count was performed to determine the growth rate (A) or the percentage of cell death (B). (C) Gli1 mRNA expression levels were determined by qRT-PCR after treatment of ASZ001 BCC cells with Glabrescione B (GlaB) or DMSO only for the indicated times. Results are expressed in arbitrary units as relative quantification normalized with endogenous control β2-microglobulin and HPRT. In all experiments data show the mean of three independent experiments. Error bars indicate SD. *P<0.05 vs DMSO.

Figure 16:
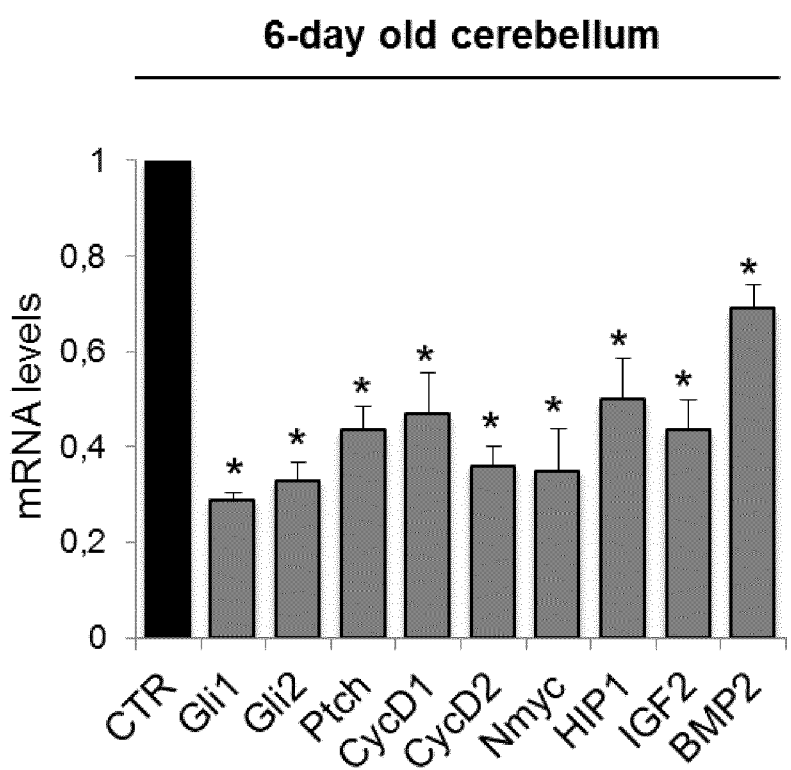

FIG. 16. qRT-PCR shows Hh targets mRNA expression levels determined in 6-day old mouse cerebellar progenitors after s.c. injections of Glabrescione B. Results are expressed in arbitrary units as relative quantification normalized with endogenous control β2-microglobulin and HPRT. Data show the mean±SD of three independent experiments. *P<0.05 vs CTR FIG. 17. Glabrescione B inhibits Gli1-dependent MB tumor growth in vivo (Ptch1$^{+/-}$ MB allografts). (A) Change of tumor volume during Glabrescione B (GlaB) or vehicle (CTR) treatment period (days 18). (B) Representative flank allografts average volumes (upper panel); representative H&E staining of tumors (middle panel); immunohistochemistry shows Ki67 staining (lower panel). (C) qRT-PCR of Gli1 and Ptch1 mRNA expression levels normalized with endogenous control β2-microglobulin and HPRT. Data show the mean±SD of tumor (n=6) for each treatment. *P<0.05 vs CTR.

Figure 18:
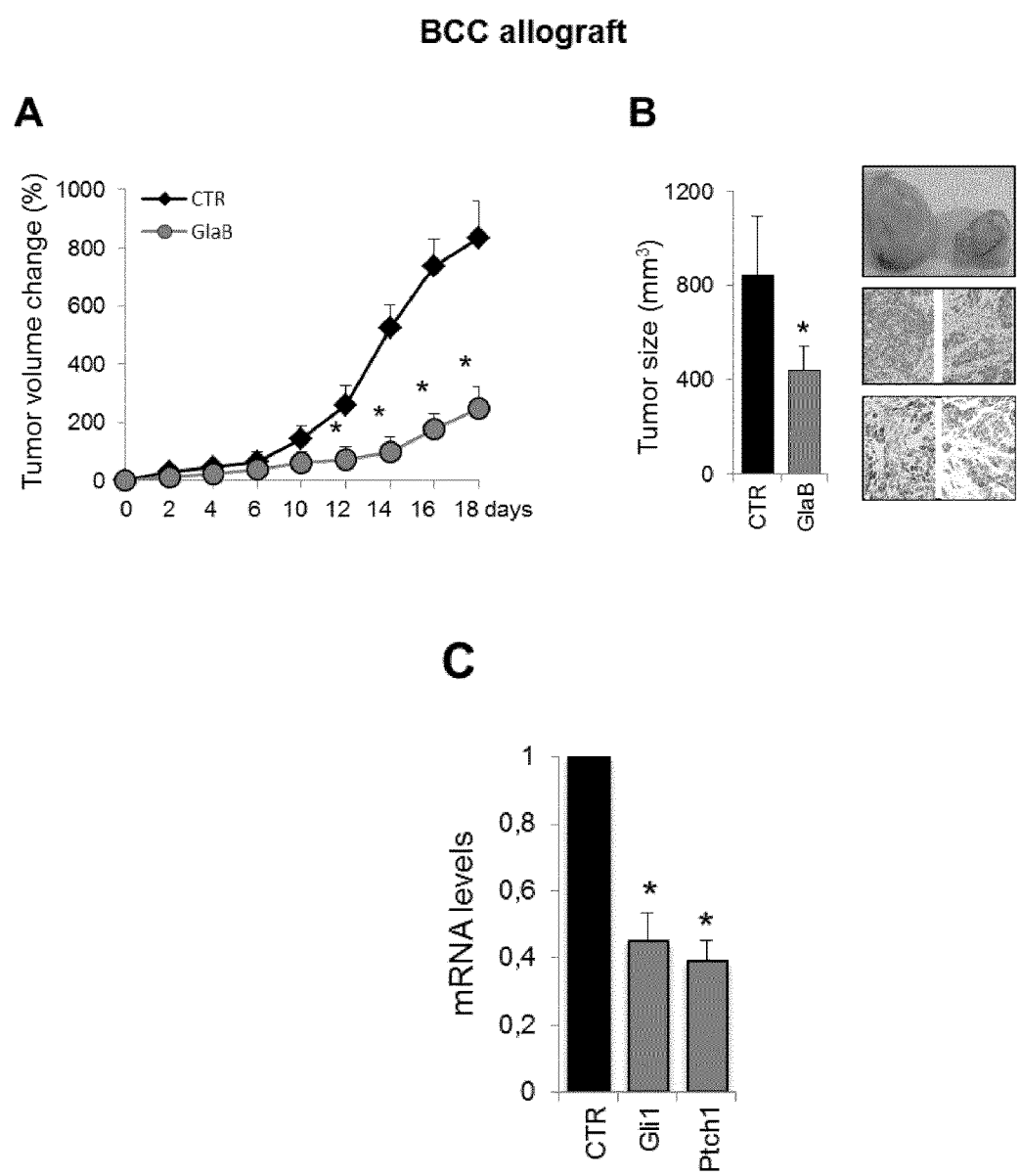

FIG. 18. Glabrescione B inhibits Gli1-dependent BCC tumor growth in vivo. (ASZ001 BCC allografts). (A) Change of tumor volume during Glabrescione B (GlaB) or vehicle (CTR) treatment period (18 days). (B) Representative flank allografts average volumes (upper panel); representative H&E staining of tumors (middle panel); immunohistochemistry shows Ki67 staining (lower panel). (C) qRT-PCR of Gli1 and Ptch1 mRNA. Shown is the mean±SD of tumor (n=6) for each treatment. *P<0.05 vs CTR.

Figure 19:
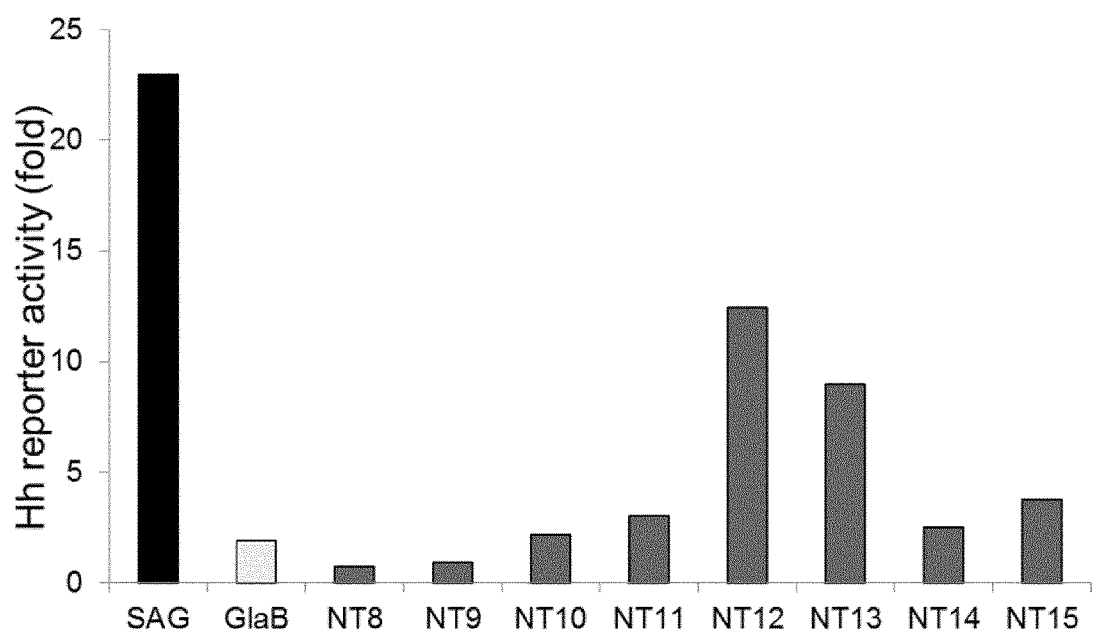

FIG. 19. Effect of derivatives NT8, NT9, NT10, NT11, NT12, NT13, NT14 and NT15 on the Hedgehog pathway, measured at 5 μM dose in a luciferase assay where the gene reporter was Gli1 and the pathway was activated by the SAG molecule, a potent SMO agonist.

DETAILED DESCRIPTION OF THE INVENTION

To discover natural compounds as inhibitors of the Hh pathway (targeting the SMO receptor and/or the Gli1 protein), two distinct computational screening protocols were established, based on the availability of structural or molecular information. A ligand-based approach was followed to search for antagonists of the SMO receptor, based on the chemical structure of potent SMO antagonists described in the literature. Moreover, a receptor-based approach was used to target Gli1, based on the availability of a crystallographic structure of Gli1-ZF in complex with DNA (PDB ID: 2GLI) (Pavletich and Pabo 1993).

In Silico Screening
Pharmacophore Generation

A training set of 9 active SMO antagonists, retrieved from the literature and from patents, was chosen to generate ligand-based pharmacophore models. Since multiple alignment schemas are allowed for selected compounds in the 3D space, multiple pharmacophores were generated accordingly by means of the "Common Feature Pharmacophore Generation" protocol implemented in the molecular modeling suite Discovery Studio 2.5 from Accelrys (Barnum, Greene et al. 1996). Pharmacophores were then scored and ranked based on their ability to map the training set and the six top-ranking pharmacophores were selected. They belong to two different groups: Type1—three hydrogen bond acceptor (HBA) and three hydrophobic (HYD) features are necessary to represent the interaction pattern of potent SMO antagonists with the SMO receptor (FIG. 1A); Type2—three HBA, two HYD and a hydrogen bond donor (HBD) features are necessary to represent the interaction pattern of potent SMO antagonists with the SMO receptor (FIG. 1B). Coordinates of pharmacophoric features and inter-feature distances are reported in Tables 1-4. It is to be specified that this training set has been already used for similar purposes (Manetti, Faure et al. 2010). However, the use of multiple pharmacophores represents a unique feature of the present invention, since in the previous attempt a single pharmacophore was used for filtering chemical libraries in searching for SMO antagonists (Manetti, Faure et al. 2010). The use of multiple pharmacophores for representing ligand binding to SMO better accounts for receptor flexibility, as well as enhances the research of chemically diverse candidate lead molecules with respect to the training set. Moreover, a HBD feature was used for the first time to represent the ligand interaction to SMO, as several known SMO antagonists are endowed with at least one HBD group.

Pharmacophoric Screening

The six pharmacophores described above were used as 3D query to filter the unique library of natural compounds, whose features are described in the example n.10. Ligand conformational analysis was performed by the CAESAR algorithm. Pharmacophore screening was performed with Discovery Studio 2.5. The Search 3D Database and the "Ligand Pharmacophore Mapping" protocols were subsequently used to filter the virtual library and to calculate the FitValue for each ligand, as a measure of how well a ligand fits a pharmacophore. Based on pharmacophore screening results, ligands were divided into three groups: 1) ligands that map all pharmacophores; 2) ligands that map only Type1 pharmacophores and 3) ligands that map only Type2 pharmacophores. A consensus "rank by rank" procedure was applied to merge results obtained by filtering through each pharmacophore model. Since the library included natural products with molecular dimension spanning from small to very large (for example, molecular volume ranges from 465.9 to 2981.8 Å$^3$, Polar Surface Area from 8.2 to 265.6 Å), with the aim of prioritizing small molecular compounds the Ligand Efficiency (LE) was further calculated for each selected compound as the ratio between the FitValue and the number of ligand heavy atoms (LE=FitValue/no. heavy atoms). 16 molecules endowed with the highest LE values were deemed top priority and selected for in vitro studies. The alignment of one exemplified compound, Glabrescione B, to a pharmacophore model is showed in FIG. 2.

Pharmacophore Refinement

Based on biological results from a luciferase assay where the gene reporter was Gli1 and the pathway was activated by the SAG molecule, a potent SMO agonist, 2 molecules were classified as highly active Hh inhibitors, showing more than 50% inhibition at 5 μM (Glabrescione B and 2,4,5,3',4'-penta-OMe Chalcone), 5 as moderately active, showing up to 30% inhibition at 30 μM (Jaceidin, Auriculasin, 3,4-di- MDO-2',4',5'-tri-OMe dihydrochalcone, 2,3,4,6,3',4'-hexa-OMe Chalcone, Martinoside,) and 9 were not active (Barbinervic Acid, Kuwanol-E, Myricetin, Sorocein-A, Sorocein-B, Isosophoranon, Veratrin, Hesperidin, Naringin). Notably, a highly comparable average molecular weight for highly active (average MW=404.45) and moderately active Hh inhibitors (average MW=390.80) was observed, whereas a significantly higher molecular weight is showed by inactive compounds (average MW=503.51). Since tested compounds were composed only by C, O and H atoms, molecular weight was considered in this case as proportional to the molecular dimension. Therefore, the inventors envisioned that compounds having a high MW were not active probably because the ligand binding site on the SMO receptor was not large enough to accommodate these substances, or they encounter steric hindrance within the SMO binding site. Reducing the steric accessibility of pharmacophore models may improve computational results. Therefore, inactive compounds were used for the steric refinement of pharmacophores by means of the "Steric Refinement with Excluded Volumes" protocol of Discovery Studio 2.5 that places excluded volumes to pharmacophore models.

Structure-Based Virtual Screening

Based on the availability of a crystal structure of the zing-finger domain of Gli1-ZF in complex with DNA, a structure-based virtual screening protocol was established to screen the unique library of natural compounds, whose features are described in the example n.10. First, MD simulations were performed to relax atoms coordinates in explicit solvent and to sample the conformational space. Four different replicas of unrestrained MD were simulated for 20 ns each, starting from slightly different initial coordinates. A representative structure was extracted from MD trajectories at the convergence and further relaxed by means of energy minimization after removal of DNA. Subsequently, molecular docking was used to predict the theoretical binding mode and affinity of natural compounds towards the representative Gli1-ZF structure refined by MD. Based on literature data, the binding site was centered on T374 that is within ZF4 and ZF5 (Sheng, et al. 2006). Compounds of the unique library were docked to Gli1-ZF by means of the GoldScore function of the GOLD program (version 5.0.1) (Verdonk, et al. 2003), which is generally recommended for binding sites particularly solvent-exposed or accounting for several H-bonding ligand-protein interactions, such as the ZF4. Further, a rescoring procedure consisting on the calculation of the ligand delta energy of binding by means of the MM-GBSA methods was applied, with the aim of decreasing as much as possible the number of false positive identified by docking. After docking and rescoring, the LE was calculated as the ratio between the delta energy of binding and the number of heavy atoms of each ligand. Interestingly, Glabrescione B that was already evaluated as SMO antagonist was found within the top ranking positions of the structure-based virtual screening. For this reason, as well as to exploit the possibility to develop a multitarget inhibitor of the Hh pathway, Glabrescione B was deemed top priority for in vitro testing. The docking-based binding mode of Glabrescione B to Gli1-ZF is showed in FIG. 3.

Pharmacology

Glabrescione B potency was evaluated by measuring its ability to inhibit Hh pathway in a cellular context of Hh signaling hyper-activation. This condition, leading to constitutive activation of Gli transcription factors, can be triggered by overexpressing Gli1 or treating Hh-responsive cell lines with Shh ligand or SAG, a potent SMO agonist or can occur in cells following mutations of key components of the pathway.

The effects of Glabrescione B as SMO and Gli1 antagonist have been examined by biochemical and in various cell-based assays.

Biochemical Assay.

Affinity of Glabrescione B and its direct binding to SMO receptor was quantified in a displacement assay. The assay is based on the use of the Bodipy-cyclopamine (BC), a fluorescent derivative of cyclopamine, which interacts with SMO at the level of its heptahelical bundle. To this end, HEK293 cells were transfected with a vector expressing SMO protein and then incubated with BC in the absence or presence of various concentrations of Glabrescione B. This assay revealed that Glabrescione B blocked BC binding to SMO in a dose-dependent manner with an $IC_{50}$ of 1 µM (FIG. 5). KAAD, used as positive control, abrogated BC binding to cell expressing SMO. Together, these results show that displacement assay is specific and demonstrate that Glabrescione B binds to SMO receptor at the level of the Bodipy-cyclopamine binding site.

Cellular Assay.

To investigate the inhibitory properties of Glabrescione B on Hh signaling, the inventors examined its effects in NIH 3T3 Shh-light II (Shh-LII) cells stably incorporating an Hh-responsive (Gli-RE) reporter, in which induction of the pathway occurs following treatment with the SMO agonist SAG. This in vitro test revealed that Glabrescione B significantly reduced luciferase activity in cells treated with SAG in a dose-dependent manner (FIG. 6) and suppressed the signaling. The $IC_{50}$ in this assay was 0.8 µM.

Efficacy of Glabrescione B to directly target Gli1 protein, the final effector of Hh pathway, was also tested. HEK293 cells transiently expressing Gli1 and a Gli-dependent luciferase reporter, showed that Glabrescione B was capable of reducing Gli1-mediated transcription in a dose-dependent manner with an $IC_{50}$ of ≈15 µM (FIG. 7). GANT61, the only small-molecule described to inhibit Gli1 function (Lauth et al., *PNAS* 104: 8455-8460), was included as positive control.

To analyze the antagonist properties of Glabrescione B under more physiological conditions, the inventors used MEF-Ptch$^{-/-}$ cells, embryo fibroblasts derived from Ptch$^{-/-}$ mouse, in which the activation of Hh signaling is consequence of Ptch1 deletion. Since Patched acts as upstream repressor of SMO, inhibition of the Hedgehog pathway from Patched is prevented and the Hedgehog pathway is constitutively activated in this cell lines, which turned out to be a reliable cellular model for studying the effect of Hedgehog inhibitors. These cells showed strongly reduced mRNA and protein levels of Gli1 (a readout of Hh signaling) when treated with Glabrescione B at different concentrations (FIGS. 8A and B). Further, authors tested the inhibitory activity of Glabrescione B on MEF-SuFu$^{-/-}$ cells, which represent another cellular model of activated Hedgehog pathway. Indeed, in this cell line aberrant Hh pathway activation is due to genetic ablation of the downstream negative regulator SuFu. Treatment of MEF-SuFu$^{-/-}$ cells with Glabrescione B led to significant reduction of the high expression levels of Gli1, as indicated by quantitative RT-PCR (FIG. 9). These results confirm that Glabrescione B is a multitarget inhibitor of Hh signaling, able to act both upstream by its direct binding to SMO receptor and downstream of SMO and SuFu by suppressing Gli1 transcription functions.

A biological assay was performed in cerebellar neural progenitors cells obtained from 4-days-old mice, when they are actively proliferating under Sonic Hedgehog (Shh) stimulus. As expected, treatment of these cells with Shh increased the proliferation rate, as evaluated by BrdU-incorporation assay. Importantly, Glabrescione B antagonized this effect (FIG. 10). To further evaluate the antiproliferative effect of Glabrescione B, human MB cell lines D283 were treated with Glabrescione B at different concentrations. MTS and BrdU incorporation assay demonstrated a dose-dependent inhibitory effect on cell proliferation following 48 h of exposure to the dose range of 1-50 µM (FIGS. 11A and B). The biomolecule was active, as shown by the growth rate inhibition (70-95%). Notably, the inhibitory effect of Glabrescione B on MB D283 cell proliferation was coupled to an increase of the percentage of cell death, in a dose-dependent manner (FIG. 12). More important, Glabrescione B was ineffective on unrelated signal transduction pathways (Wnt/Bcatenin and Jun/AP1activation; 0% inhibition at 30 µM of Glabrescione B), demonstrating a high degree of selectivity for Hh signaling.

Hh activity preferentially associates to stemness features. For this reason, the Hh pathway antagonist Glabrescione B has also been investigated for its ability to modulate the behavior of MB cancer stem cells (CSCs). Analysis by quantitative RT-PCR revealed an inhibitory effect of Glabrescione B on Hh activity, as showed by reduction of Gli1 mRNA levels (FIG. 13). Further, treatment with Glabrescione B had a suppressive effect on MB CSCs self-renewal, in particular on the percentage of neurospheres-forming cells derived from murine $Ptch^{+/-}$ MB (condition of Hh pathway constitutive activation). Notably, this inhibitory effect was significantly higher than the effect achieved with known Hh antagonist, as KAAD (FIG. 14).

Chemical Synthesis of the Bioactive Substances

Abbreviations used in the description of the chemistry and in the examples that follow are: MD: Molecular Dynamics; MM-GBSA: Molecular Mechanics Generalized Born Surface Area; Gli1-ZF: zinc finger domain of Gli1; BrdU: 5'-bromo-2Ldeoxy-uridine; DMSO: dimethyl sulfoxide; MeOH: methanol; EtOH: ethanol; EtOAc: ethyl acetate; EDTA: Ethylenediaminetetraacetic acid; HBSS: Hank's Balanced Salt Solution; HPRT: Hypoxanthine-guanine phosphoribosyl transferase; cyclopamine-KAAD: 3-Keto-N— (aminoethyl-aminocaproyl-dihydrocinnamoyl)-cyclopamine; M: molar; min: minutes; h: hour(s); g (grams); µL (microliters); mL (milliliters); mmol (millimoles); nm (nanometers); µM (micromolar); r.t.: room temperature; RT-QPCR: quantitative real time PCR; Gli-luc: Gli-dependent luciferase reporter, ESI (Electron Spray Ionization).

Except where indicated otherwise, all temperatures are expressed in ° C. (degrees centigrade) or K (Kelvin).

$^1$H NMR and $^{13}$C NMR spectra were recorded using a Bruker 400 Ultra Shield™ spectrometer (operating at 400 MHz for $^1$H and 100 MHz for $^{13}$C) using tetramethylsilane (TMS) as internal standard. Chemical shifts are reported in parts per million (ppm). Signals for —NCH3 carbon are not present in the $^{13}$C NMR data.

The chemical shifts are expressed in parts per million (ppm, δ units). The coupling constants are expressed in Hertz (Hz) and the splitting patterns are described as s (singlet), bs (broad signal), d (doublet), t (triplet), q (quartet), quint (quintet), m (multiplet).

Mass spectrometry was performed using a Thermo Finnigan LXQ linear ion trap mass spectrometer, equipped with an electrospray ionization (ESI) ion source. High-resolution mass spectra (HRMS) were obtained using a Bruker BioApex Fourier transform ion cyclotron resonance (FT-ICR) spectrometer fitted with an ESI source.

Example n. 1: Displacement Assay with Bodipy-Cyclopamine

To investigate the binding properties of Glabrescione B to SMO receptor, a competition assay was carried out. In this experiment it was analyzed whether Glabrescione B could compete with Bodipy-cyclopamine (BC; 5 nM USBiological, cat. # B2527), a fluorescent derivative of cyclopamine, which is known to interact with the SMO receptor at the level of its heptahelical bundle. To this aim, HEK293 cells (ATCC, cat. # CRL-1573) were transfected with SMO expression vector (Chen et al, 2002) by using Lipofectamine 2000 (Invitrogen, cat #11668-019); 24 h after transfection the cells were fixed in paraformaldehyde 4% and incubated with 5 nM BC alone or in presence of increasing amounts of Glabrescione B for 2 h at 37° C. The cells were also treated with the steroidal alkaloid SMO antagonist cyclopamine-KAAD (3-Keto-N-(aminoethyl-aminocaproyl-dihydrocinnamoyl)-cyclopamine, 1 µM Calbiochem, cat. #239804) a chemical analogous of cyclopamine, included as positive control. Cells were analyzed with a Carl Zeiss microscope (Axio Observer ZI). Cell cultures images were taken with a 20× objective for the analysis. Bodipy-cyclopamine (green) and DAPI (blue) signals were analyzed in 3-4 representative fields for coverslips. The result showed in FIG. 5 indicates that Glabrescione B abrogated BC binding to cells expressing SMO with an $IC_{50}$ of 1 µM by interacting with SMO receptor.

Example n. 2: Effects of Glabrescione B on Hh Signaling

The ability of Glabrescione B to suppress Hh signaling was assessed in a cellular context of Hh pathway induction. To this end, the antagonist properties of Glabrescione B were determined in Shh Light II (ATCC, cat. # CRL-2795), a murine fibroblast NIH 3T3 cell line. These cells, stably incorporating the Gli-luc reporter and the pRL-TK Renilla reniformis (as described in Taipale, Chen et al. 2000) are a standard tool used to assay Hh pathway activity. The cells that reached the confluence were treated for 48 h with the SMO agonist SAG (200 nM, Alexis, cat. #ALX-270-426-M001) in absence or in presence of Glabrescione B at the amount indicated in FIG. 6. SAG is a potent cell-permeable benzothiophene compound that promotes the coupling of SMO with its downstream effector by interacting with the SMO heptahelical domain ($K_d$=59 nM) and shown to induce Hedgehog pathway activation. Control cells were treated with only DMSO (0.5%, SERVA, cat. #39757.02) Determination of luciferase activities was carried out using the Dual-Luciferase assay according to manufacturer's instructions (Dual-Luciferase® Reporter assay system; Promega, cat. # E1980). All presented data are firefly luciferase activity reported to the Renilla control activity. As shown in FIG. 6, Glabrescione B inhibits Hh signaling upon SAG activation, as evidenced by the dose-dependent decrease in luciferase reporter activity. $IC_{50}$ of 0.8 µM, represents the concentration of Glabrescione B necessary to have fifty percent of inhibition.

Example n. 3: Inhibition of Gli1-Mediated Transcription in HEK293 Cells

To investigate the ability of Glabrescione B to block downstream Hh signaling by targeting Gli1 protein functions, the inventors performed a luciferase assay in HEK293 cells transiently expressing Gli1. The cells were seeded in 24-multiwell plates and the day after transfected with Gli1 expression vector together with the reporter plasmids 12×GliBS-Luc and pRL-TK *Renilla reniformis* (Kogerman P et al, 1999; Everett L et al, 1999). Twenty-four hours later, Glabrescione B was added at different concentration as indicated and GANT61 (included as positive control, Enzo Life Science, cat. # ALX-270-482) was added at the final concentration of 20 µM in DMSO (0.5%, SERVA, cat. #39757.02). After 24 h of treatment cells were lysed and analyzed by using the Dual Luciferase kit according to manufacturer's instructions (Dual-Luciferase® Reporter assay system; Promega, cat. # E1980). All presented data are firefly luciferase activity reported to the *Renilla* control activity. As shown in FIG. 7, Glabrescione B was capable of interfering with Gli1-induced transcription in a dose-dependent manner and similarly to GANT61.

Example n. 4: Effects of Glabrescione B on Hh Responsive Cell Line

In order to determine whether Glabrescione B regulates cells with a constitutive Hh pathway activation, the MEF-Ptch$^{-/-}$ cell line (a kind gift by M. Scott, Stanford University, CA, in which the activation of Hh signaling is consequence of Ptch1 deletion, Goodrich, L. V. et al, 1997) was treated with Glabrescione B at different concentrations and the effect on expression of Hh/Gli1 pathway was determined by quantitative RT-PCR and western blot analysis. Total RNA was isolated with TRI Reagent (Invitrogen, cat. # AM9738) and reverse transcribed with Superscript II reverse transcriptase (Invitrogen, cat. # PN100004925) and random hexamers (Invitrogen, cat. # PN58875). Quantitative PCR (QPCR) analysis of Gli1 mRNA expression was performed on each cDNA sample using the ABI Prism 7900 Sequence Detection System employing Assay-on-Demand Reagents (Life Technologies). A reaction mixture containing cDNA template, TaqMan Universal PCR master mix (ABI) and primer probe mixture was amplified using standard QPCR thermal cycler parameters. Each amplification reaction was performed in triplicate and the average of the three threshold cycles was used to calculate the amount of transcript in the sample (using SDS version 2.3 software). All values were normalized with HPRT (Hypoxanthine-guanine phosphoribosyl transferase) endogenous controls (Life Technologies, cat. # Mm 00494645_m1 Gli1; Mm 01545399_m1). For western blot analysis, cells were lysed in Tris-HCl (pH 7.6) 50 mM, NaCl 150 mM, NP-40 1%, EDTA 5 mM, deoxycholic acid sodium salt 0.5%, NaF 100 mM and protease inhibitors. The lysates were centrifuged at 13,000 g for 20 minutes, separated by a 8% SDS-PAGE and transferred to a nitrocellulose membrane. Immunoblotting, was performed with a mouse monoclonal antibody against Gli1 (Cell Signaling, cat. # L42B10) or goat polyclonal antibody against Actin (Santa Cruz Biotechnology, cat. #11012), used as loading control. HRP-conjugated secondary antibody anti-mouse or anti-goat IgG (Santa Cruz Biotechnology, cat. # SC-2005, # SC-2020) were used, and immunoreactive bands were visualized by enhanced chemiluminescence (Perkin Elmer, cat. # NEL105001EA). KAAD (1 µM, Calbiochem, cat. #239804) was used as control. As shown in FIG. 8, Glabrescione B down-regulates Gli1 expression compared to the untreated control.

To further elucidate the concept of downstream pathway inhibition by Glabrescione B, the inventors used MEF-SuFu$^{-/-}$ cells (a kind gift by R. Toftgard, Karolinska Institutet, Sweden, Svärd, J. et al, 2006), in which the downstream Hh pathway activation is consequence of SuFu genetic ablation. Confluent cells were treated with Glabrescione B at the amount indicated in the FIG. 9 and Gli1 expression levels were determined by quantitative RT-PCR as previously described. As shown in FIG. 9, Glabrescione B promoted a significant downregulation of mRNA Gli1 levels. Data were normalized with HPRT endogenous controls, as described above. These findings confirm that Glabrescione B is indeed inhibitor of Hh signaling downstream of SMO and SuFu.

Another experiment to assess whether Glabrescione B also regulates Hh pathway in a physiological context was carried out in cerebellar granule cells precursors (GCPs) isolated from 4-days-old mice according to established protocols (Wechsler-Reya and Scott, 1999). Briefly, cerebella were removed aseptically, cut into small pieces, and incubated at room temperature for 15 min in digestion buffer [Dulbecco's PBS (Invitrogen, Gaithersburg, Md.) with 0.1% trypsin, 0.2% EDTA, and 100 µg/ml DNase]. Tissues were then triturated with fire-polished Pasteur pipettes to obtain a single-cell suspension. Cells were centrifuged, resuspended in Neurobasal medium supplemented with B27, penicillin-streptomycin, and L-glutamine (2 mM) (Invitrogen) and plated at a density of $8\times10^5$ cells/cm$^2$ on tissue-culture dishes or eight-well Lab-Tek chamber slides (Permanox slide; Nunc, cat. #177445) coated with 1 mg/ml poly-L-lysine. These cells were treated with Shh alone (Recombinant mouse Sonic Hedgehog, amino-terminal peptide; 3 µg/ml, R&D system, cat. #461-SH) or in combination with different concentration of Glabrescione B for 48 h and growth inhibition IC$_{50}$ doses were determined by BrdU (bromodeoxyuridine, 5'-bromo-2Ldeoxy-uridine, Roche, cat. #11 296 736 001) labeling assay according to standard methods (FIG. 10). After BrdU incorporation, GCPs were fixed in 4% paraformaldehyde for 20 min at room temperature, incubated in 0.2% Triton X-100 to permeabilize cells and treated with 2N HCl to denature DNA. BrdU detection was performed according to the manufacturer's instructions.

In order to determine whether Glabrescione B also inhibits the proliferation of cancer cells, human MB D283 cells (ATCC, cat. #HTB-185) were treated with Glabrescione B and proliferation/viability rate were measured by BrdU incorporation and MTS assays, respectively. Cells, as shown in FIG. 11, displayed a dose-dependent inhibitory effect on cell proliferation (FIG. 11A) and viability (FIG. 11B) following 48 h of exposure to the dose range of 1-50 µM. More important, Glabrescione B was able to promote cell death of D283 MB cells, as reported by Trypan Blue count assay (FIG. 12). Cell proliferation was evaluated by a BrdU-labelling assay (8 h pulse; Roche, cat. #11 296 736 001) as described above; cell viability was evaluated by MTS (a tetrazolium compound [3-(4,5-dimethylthiazol-2-yl)-5-(3-carboxymethoxyphenyl)-2-(4-sulfophenyl)-2H-tetrazolium, inner salt; MTS; Promega, cat. #G3580). Cell death was measured by Trypan Blue (Sigma, cat. #T8154) exclusion counting at least 200 cells, in duplicate samples. All described assays were evaluated at 48 h after treatment.

Example n. 5: Effects of Glabrescione B on MB Cancer Stem Cells and Cancer-Derived Stem-Like Cells It has been described that Hh activity preferentially associates to stemness features. In order to determine whether Glabrescione B also modulates the behavior of MB cancer stem cells (CSCs), neurospheres isolated from murine Ptch$^{+/-}$ MB were treated with Glabrescione B for 48 h and the levels of Gli1 were determined by quantitative RT-PCR.

Murine MBs were isolated from Ptch1$^{+/-}$ mice (Goodrich, Milenkivic et al. 1997). Tissues were collected in HBSS supplemented with 0.5% glucose and penicillin-streptomycin, grossly triturated with serological pipette and treated with DNAse I to a final concentration of 0.04% for 20 min. Finally, cells aggregates were mechanically dissociated using pipettes of decreasing bore size to obtain a single cell suspension. CSCs were cultured as neurospheres in selective medium after centrifugation, DMEM/F12 supplemented with 0.6% glucose, 25 mg/ml insulin, 60 mg/ml N-acetyl-L-cystein, 2 mg/ml heparin, 20 ng/ml EGF, 20 ng/ml bFGF, 1× penicillin-streptomycin and B27 supplement without vitamin A. Neurospheres were treated with the steroidal alkaloid SMO antagonist, cyclopamine-KAAD (1 µM Calbiochem, cat. #239804). RNA extraction and mRNA expression analysis were performed as described above. As shown in FIG. 13, Gli1 expression was down-regulated compared to the untreated control. All values were normalized with HPRT internal controls.

Another experiment was carried out to determine the ability of Glabrescione B to suppress MB CSCs self-renewal. To this aim neurospheres derived from murine Ptch$^{+/-}$ MB were treated with Glabrescione B at different concentrations and the percentage of neurospheres-forming cells was measured. For the neurosphere forming assay, cells were plated at clonal density (1-2 cells/mm2) into 96-well plates and cultured in selective medium as described above.

The results shown in FIG. 14 indicate that Glabrescione B has an inhibitory effect on self-renewal of cancer stem cells. Notably, this inhibitory effect was significantly higher than the effect achieved with known Hh antagonist KAAD, thus reinforcing that Glabrescione B is a potent inhibitor of tumor growth via inhibition of the Hh signaling pathway.

Similar results were observed in ASZ001 basal cell carcinoma cells (BCC), previously characterized as an Hh/Gli-dependent tumor cell line harbouring Ptch1 deletion (Aszterbaum et al, 1999). Total RNA was isolated with Trizol (Invitrogen, Eugene, Or, USA) and reverse transcribed with Superscript II reverse transcriptase and random hexamers (Invitrogen, Eugene, Or, USA). Quantitative real-time PCR (qRT-PCR) analysis of Gli1, Gli2, Ptch1, Ptch2, Nanog, Oct-4, Cyclin D1, Cyclin D2, Nmyc, HIP1, Sfrp1, Bmp2, IGF2, β-2 microglobulin, HPRT, mRNA expression was performed on each cDNA sample using the ABI Prism 7900HT Sequence Detection System employing Assay-on-Demand Reagents (Applied Biosystems, Foster City, Calif., USA). A reaction mixture containing cDNA template, TaqMan Universal PCR master mix (Applied Biosystems, Foster City, Calif., USA) and primer probe mixture was amplified using standard qRT-PCR thermal cycler parameters. Each amplification reaction was performed in triplicate and the average of the three threshold cycles was used to calculate the amount of transcript in the sample (using SDS version 2.3 software). mRNA quantification was expressed, in arbitrary units, as the ratio of the sample quantity to the quantity of the calibrator. All values were normalized with two endogenous controls, β-2 microglobulin and HPRT, which yielded similar results.

BCC cell proliferation was impaired by in vitro treatment with Glabrescione B together with a suppression of Gli1 mRNA before a drug-induced cell death occurred (FIG. 15). Notably, no effect was observed in Hh-independent HepG2 hepatocellular carcinoma cells or Jurkat T leukemia cells, which display undetectable levels of Gli1 (Lauth et al, 2007).

In summary, the inhibitory activity of Glabrescione B on the subset of both normal and tumor progenitor/stem cells as well as the whole tumor cell populations, is restricted to Hh/Gli-dependent cells.

Example n. 6: Glabrescione B Inhibits Gli1-Dependent Tumor Growth In Vivo

To assess the in vivo activity of Glabrescione B, we first tested its ability to suppress Hh signaling in 6-day old mouse cerebellar progenitors, considered the cell of origin of MB. 6-day old CD1 mice were randomly divided into two groups (n=6) and injected s.c. with solvent only (2-hydroxypropyl-β-cyclodextrin:ethanol, 3:1) or Glabrescione B in solvent (100 µmol/Kg) for 2 days (2-hydroxypropyl-β-cyclodextrin was purchased from Sigma Aldrich, St. Louis, Mo., USA). Cerebella were collected and mRNA levels were determined by qRT-PCR. Glabrescione B treatment reduced significantly the cerebellar levels of Hh target genes (FIG. 16).

Therefore, to verify the Glabrescione B efficacy to inhibit Hh-dependent tumor cell growth in vivo, we turned to an allograft model of MB cells. Spontaneous Medulloblastomas from Ptch1$^{+/-}$ mice were isolated, minced, pipetted to obtain a single-cell suspension and grafted s.c. at the posterior flank of female BALB/c nude mice (nu/nu) (Charles River Laboratories, Lecco, Italy). Tumors were grown until a median size of ~100 mm$^3$. Animals were randomly divided into two groups (n=6) and treated with solvent only (2-hydroxypropyl-β-cyclodextrin:ethanol, 3:1) or Glabrescione B in solvent (75 µmol/Kg) for 18 days (2-hydroxypropyl-β-cyclodextrin was purchased from Sigma Aldrich, St. Louis, Mo., USA). 2×10$^6$ ASZ001 BCC cells were resuspended in an equal volume of 154CF medium and Matrigel (BD Biosciences, Heidelberg, Germany) and injected s.c. at the posterior flank of female NOD/SCID mice (Charles River Laboratories, Lecco, Italy), as previously described (Eberl et al, 2012). Tumors were grown until a median size of ~200 mm$^3$. Animals were randomly divided into two groups (n=6) and treated with solvent only (2-hydroxypropyl-β-cyclodextrin:ethanol, 3:1) or Glabrescione B in solvent (100 µmol/Kg) for 18 days. Tumor volumes change was calculated by the formula length×width×0.5×(length+width) (Lauth et al, 2007).

Figure 17:
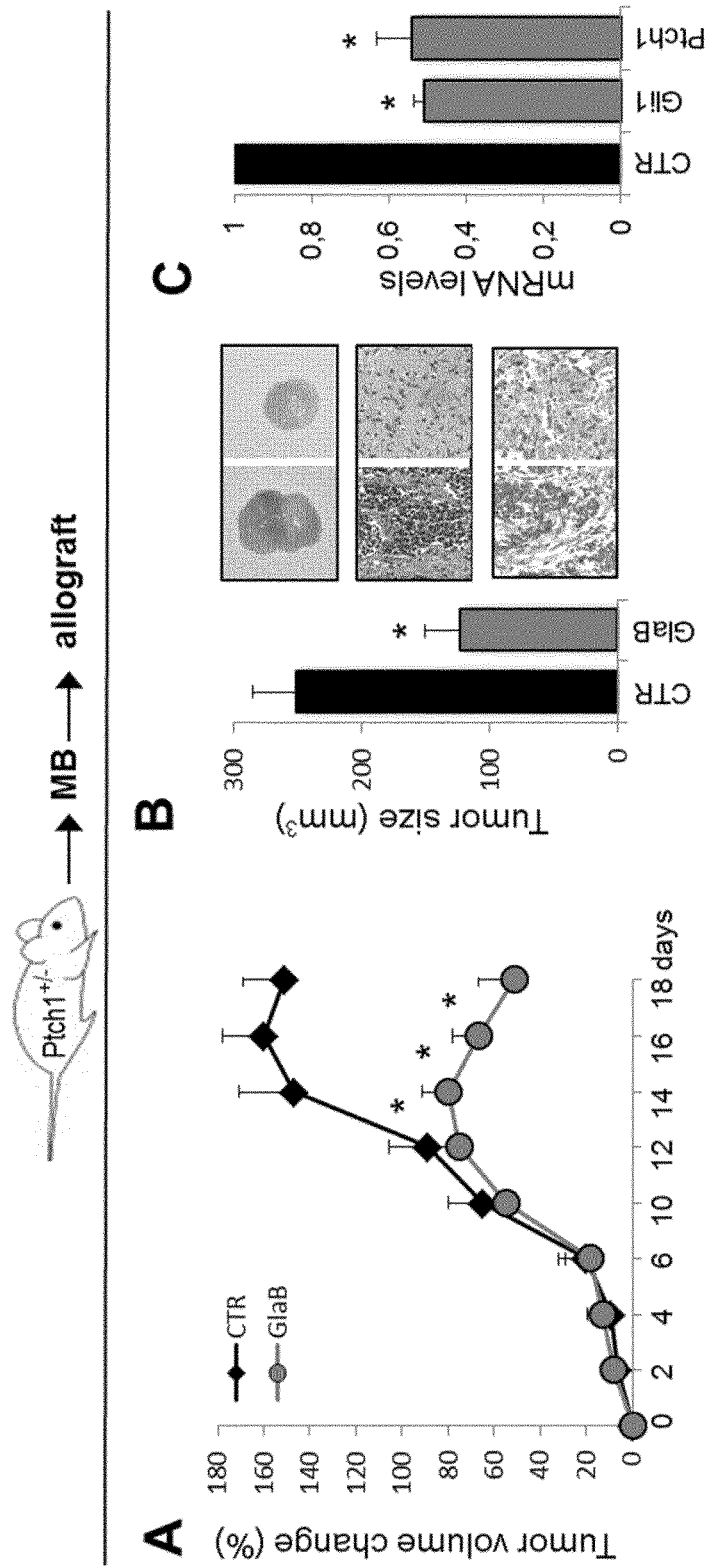

Nude mice were grafted with spontaneous primary MB from Ptch1$^{+/-}$ mice and treated every second day with s.c. injections of Glabrescione B at a concentration of 75 µmol/Kg or solvent only (n=6 for each group). During an 18-day treatment period Glabrescione B significantly suppressed tumor mass compared with controls, as confirmed by in vivo decreased Ki67 staining in Glabrescione B-treated tumors together with a reduction of Gli1 mRNA levels (FIG. 17). Notably, in vivo Glabrescione B-induced tumor growth inhibition was also observed in BCC s.c. allografts. A significant reduction of tumor growth, as well as Gli1 mRNA levels were observed 18 days after administration of Glabrescione B (100 µmol/Kg) compared to solvent alone (FIG. 18).

Example n. 7: Chemical Synthesis of Glabrescione B

The total synthesis of the isoflavone Glabrescione B is a six-step synthetic route, with an overall yield of 7%. It also permits the preparation of numerous derivatives of Glabrescione B. The use of Pd EnCat™40, as catalyst, introduces an aspect of green chemistry into the synthesis.

The yields were calculated assuming that products were 100% pure if not stated otherwise.

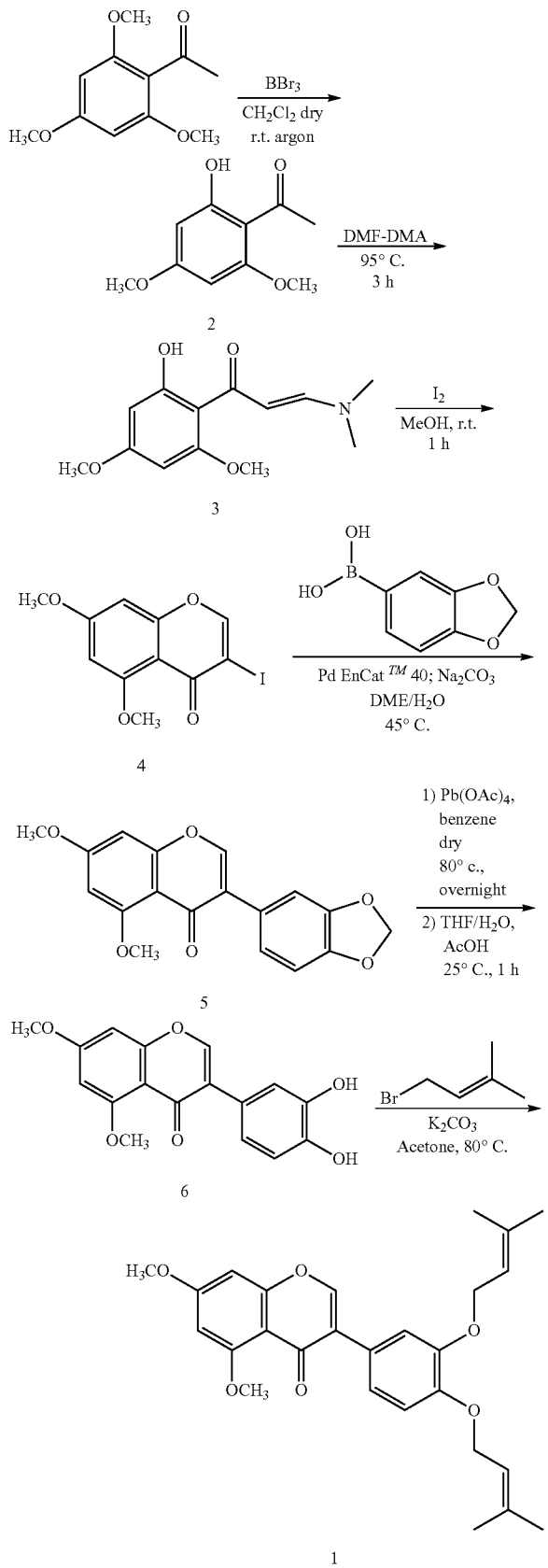

Intermediate 2:
2-hydroxy-4,6-dimethoxyacetophenone (2)

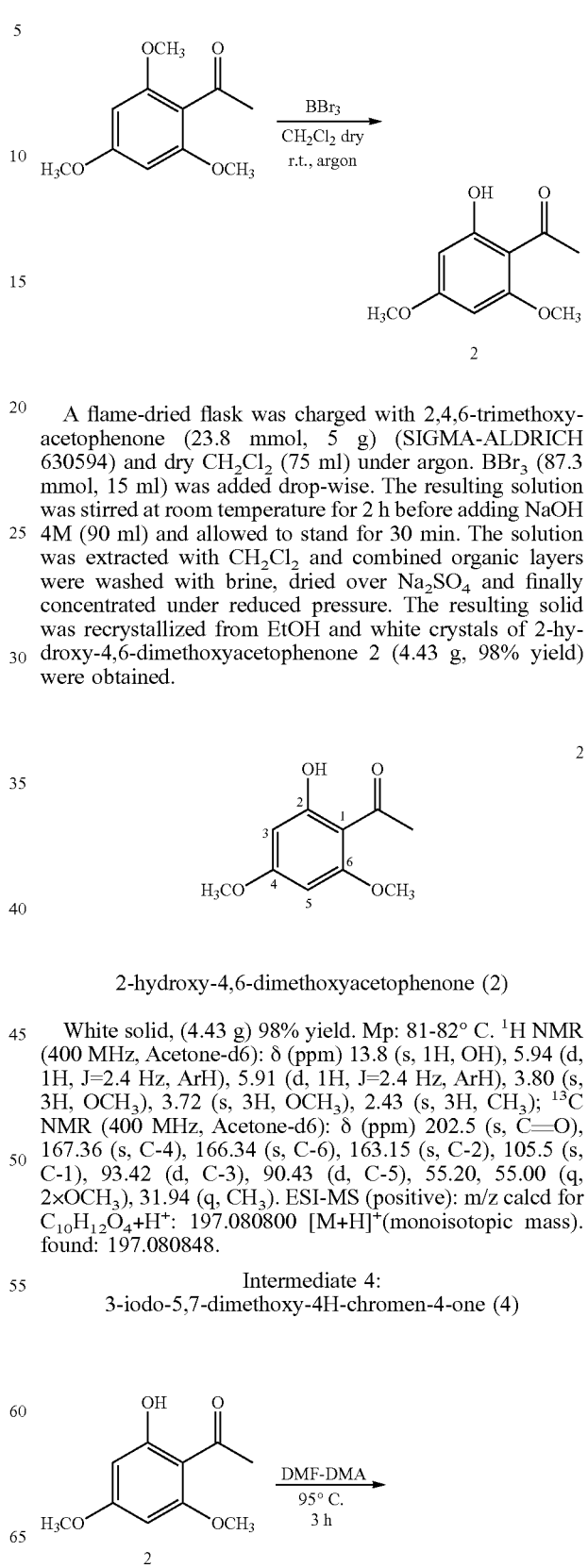

A flame-dried flask was charged with 2,4,6-trimethoxyacetophenone (23.8 mmol, 5 g) (SIGMA-ALDRICH 630594) and dry $CH_2Cl_2$ (75 ml) under argon. $BBr_3$ (87.3 mmol, 15 ml) was added drop-wise. The resulting solution was stirred at room temperature for 2 h before adding NaOH 4M (90 ml) and allowed to stand for 30 min. The solution was extracted with $CH_2Cl_2$ and combined organic layers were washed with brine, dried over $Na_2SO_4$ and finally concentrated under reduced pressure. The resulting solid was recrystallized from EtOH and white crystals of 2-hydroxy-4,6-dimethoxyacetophenone 2 (4.43 g, 98% yield) were obtained.

2-hydroxy-4,6-dimethoxyacetophenone (2)

White solid, (4.43 g) 98% yield. Mp: 81-82° C. $^1H$ NMR (400 MHz, Acetone-d6): δ (ppm) 13.8 (s, 1H, OH), 5.94 (d, 1H, J=2.4 Hz, ArH), 5.91 (d, 1H, J=2.4 Hz, ArH), 3.80 (s, 3H, $OCH_3$), 3.72 (s, 3H, $OCH_3$), 2.43 (s, 3H, $CH_3$); $^{13}C$ NMR (400 MHz, Acetone-d6): δ (ppm) 202.5 (s, C=O), 167.36 (s, C-4), 166.34 (s, C-6), 163.15 (s, C-2), 105.5 (s, C-1), 93.42 (d, C-3), 90.43 (d, C-5), 55.20, 55.00 (q, 2×$OCH_3$), 31.94 (q, $CH_3$). ESI-MS (positive): m/z calcd for $C_{10}H_{12}O_4+H^+$: 197.080800 $[M+H]^+$(monoisotopic mass). found: 197.080848.

Intermediate 4:
3-iodo-5,7-dimethoxy-4H-chromen-4-one (4)

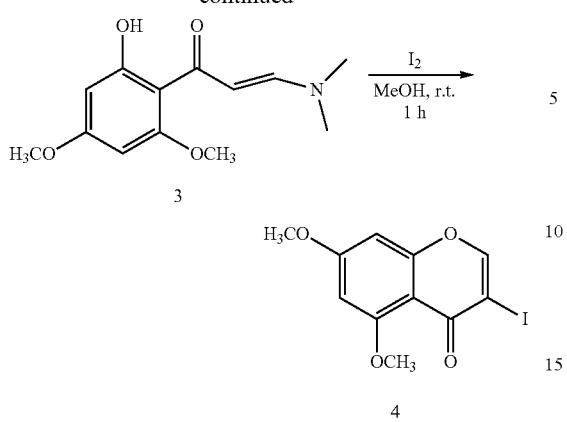

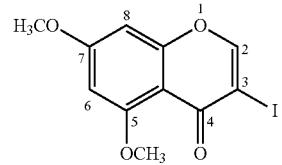

3-iodo-5,7-dimethoxy-4H-chromen-4-one (4)

White solid, (2.5 g) 33% yield. Mp: 156-157° C. $^1$H NMR (400 MHz, CDCl$_3$): δ (ppm) 8.02 (s, 1H, H-2), 6.37 (d, J=2.0 Hz, 1H, ArH), 6.32 (d, J=2.0 Hz, 1H, ArH), 3.87 (s, 3H, OCH$_3$), 3.82 (s, 3H, OCH$_3$); $^{13}$C NMR (400 MHz, CDCl$_3$): δ (ppm) 183.43 (s, C=O), 164.28 (s, C-7), 160.97 (s, C-5), 159.81 (s, C-9), 155.33 (d, C-2), 107.53 (s, C-10), 96.59 (d, C-8), 92.44 (d, C-6), 89.71 (d, =CH—I), 56.41, 55.79 (q, 2×OCH$_3$). ESI-MS (positive): m/z calcd for C$_{11}$H$_9$O$_4$I+H$^+$: 332.961800 [M+H]$^+$(monoisotopic mass). found: 332.961633.

Intermediate 5: 3-(3',4'-methylendioxyphenyl)-5,7-dimethoxy-4H-chromen-4-one (5)

A mixture of 2-hydroxy-4,6-dimethoxyacetophenone 2 (23.1 mmol, 4.5 g) and N,N-dimethylformamide dimethylacetal (97.1 mmol, 13 ml) was stirred at 95° C. for 3 h, then concentrated in vacuo to give enamino ketone 3 (5.8 g) in quantitative yield. (Biegasiewicz, St Denis et al. 2010) Compound 3 was dissolved in MeOH (450 ml) and I$_2$ (46.2 mmol, 11.7 g) was added to the solution. The mixture was stirred at room temperature for 1 h, then the solvent was evaporated. To remove residual I$_2$, the crude was treated with a saturated aqueous Na$_2$S$_2$O$_3$ solution until the mixture became clear. The mixture was then extracted with CHCl$_3$, the combined organic layers were dried over Na$_2$SO$_4$ and concentrated under reduced pressure. The residue was purified by column chromatography using hexane-EtOAc as eluent to obtain 3-iodo-5,7-dimethoxy-4H-chromen-4-one 4 (2.5 g, 33% yield) as a white powder.

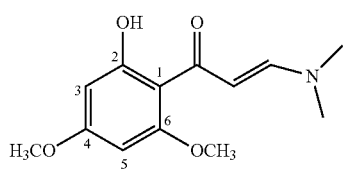

3-dimethylamino-1-(2-hydroxy-4,6-dimethoxyphenyl)propenone (3)

Red solid, (5.8 g) quantitative yield. Mp: 145-147° C. $^1$H NMR (400 MHz, CDCl$_3$): δ (ppm) 15.65 (s, 1H, OH), 7.92 (d, 1H, J=12 Hz, =CH—N), 6.25 (d, 1H, J=12.0 Hz, =CH—(CO)), 6.07 (d, 1H, J=2.4 Hz, ArH), 5.91 (d, 1H, J=2.4 Hz, ArH), 3.84 (s, 3H, OCH$_3$), 3.80 (s, 3H, OCH$_3$), 3.15 (s, 3H, NCH$_3$), 2.92 (s, 3H, NCH$_3$); $^{13}$C NMR (400 MHz, CDCl$_3$): δ (ppm) 191.64 (s, C=O), 169.00 (s, C-4), 165.54 (s, C-6), 162.86 (s, C-2), 155.83 (d, =CH—N), 106.58 (s, C-1), 96.27 (d, =CH—(CO)), 95.59 (d, C-3), 92.06 (d, C-5), 57.09, 56.57 (q, 2×OCH$_3$). ESI-MS (positive): m/z calcd for C$_{13}$H$_{17}$O$_4$+H$^+$: 252.1 [M+H]$^+$(monoisotopic mass). found: 252.1.

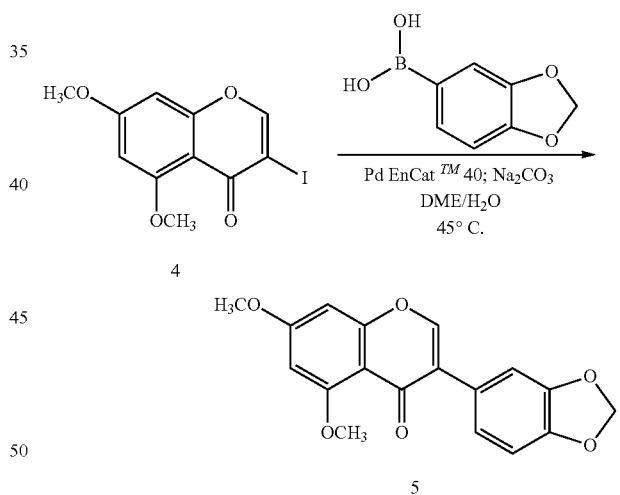

To a solution of 4 (7.5 mmol, 2.5 g) in 1,2-dimethoxyethane/H$_2$O=50:50 (150 ml) were added Na$_2$CO$_3$ (30 mmol, 3.18 g), 3,4-(methylenedioxy)-phenylboronic acid (11 mmol, 1.8 g), and Pd EnCat™40 (937 mg, 5%). The resulting mixture was stirred at 45° C. for 2 h and then filtered. The catalyst was washed with H$_2$O and CH$_2$Cl$_2$. The aqueous phase was extracted with CH$_2$Cl$_2$. The combined organic layers were dried over Na$_2$SO$_4$ and concentrated under reduced pressure. The crude residue was purified by flash chromatography to give 3-(3',4'-methylendioxyphenyl)-5,7-dimethoxy-4H-chromen-4-one 5 (1.4 g, 57% yield) as gray powder.

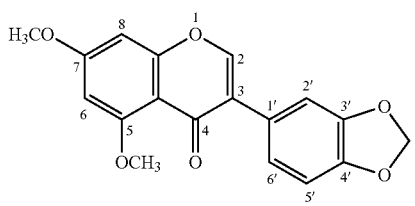

3-(3',4'-methylendioxyphenyl)-5,7-dimethoxy-4H-chromen-4-one (5)

Gray solid, (1.4 g) 57% yield. Mp: 155-156° C. $^1$H NMR (400 MHz, CDCl$_3$): δ (ppm) 7.75 (s, 1H, H-2), 7.1 (d, J=2.0 Hz, 1H, H-2'), 6.94 (dd, J=8.0 Hz and 2.0 Hz, 1H, H-6'), 6.83 (d, J=8.0 Hz, 1H, H-5'), 6.44 (d, J=2.2 Hz, 1H, H-6), 6.37 (d, J=2.2 Hz, 1H, H-8), 5.97 (broad s, 2H, O—CH$_2$—O), 3.94 (s, 3H, OCH$_3$), 3.89 (s, 3H, OCH$_3$); $^{13}$C NMR (400 MHz, CDCl$_3$): δ (ppm)=175.09 (s, C=O), 164.02 (s, C-7), 161.54 (s, C-5), 160.30 (s, C-9), 150.05 (d, C-2), 147.58 (s, C-3'), 147.58 (s, C-4'), 126.5 (s, C-3), 126.04 (s, C-1'), 122.84 (d, C-6'), 110.50 (d, C-2'), 110.0 (s, C-10), 108.35 (d, C-5'), 101.30 (t, O—CH$_2$—O), 96.74 (d, C-6), 92.73 (d, C-8), 56.41, 55.79 (q, 2×OCH$_3$). ESI-MS (positive): m/z calcd for C$_{18}$H$_{14}$O$_6$+H$^+$: 327.086300 [M+H]$^+$(monoisotopic mass). found: 327.086206.

Intermediate 6: 3-(3',4'-dihydroxyphenyl)-5,7-dimethoxy-4H-chromen-4-one (6)

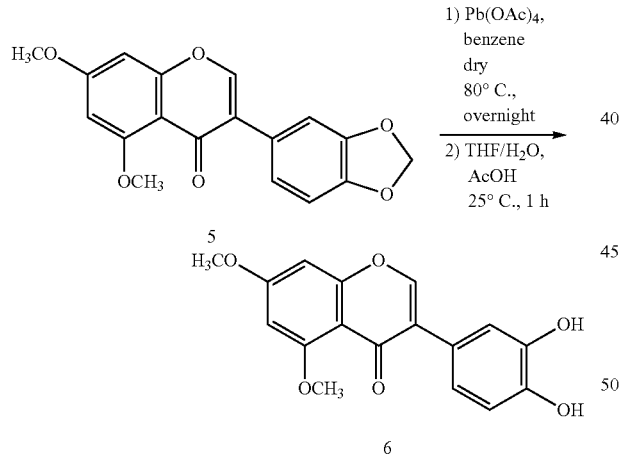

A mixture of 5 (4.3 mmol, 1.4 g) and Pb(OAc)$_4$ (17 mmol, 7.5 g, freshly recrystallized from AcOH) in dry C$_6$H$_6$ (100 ml) was stirred at 80° C. under argon overnight. After, being cooled to room temperature, the reaction mixture was filtered through a pad of Celite, washed with CH$_2$Cl$_2$ and concentrated under reduced pressure. The crude was diluted with THF/H$_2$O=5:1 (50 ml) and CH$_3$COOH (50 ml) and the resulting mixture was stirred at room temperature for 6 h. (Ye, Koshino et al. 2009) Afterwards, a saturated aqueous NaHCO$_3$ solution was added until pH 8 and extracted with EtOAc. To the combined organic layers was added a solution of NaOH 0.1 M. Water layer was treated with CH$_3$COOH and then extracted with EtOAc. The combined organic layers were dried over Na$_2$SO$_4$ and concentrated under reduced pressure to obtain 3-(3',4'-dihydroxyphenyl)-5,7-dimethoxy-4H-chromen-4-one 6 (570 mg, 42% yield).

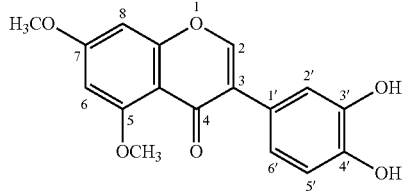

3-(3',4'-dihydroxyphenyl)-5,7-dimethoxy-4H-chromen-4-one (6)

Yellow solid, (570 mg) 42% yield. Mp: 127-129° C. $^1$H NMR (400 MHz, MeOD): δ (ppm) 7.86 (s, 1H, H-2), 6.88 (broad s, 1H, H-2'), 6.70 (broad s, 2H, H-5' and H-6'), 6.50 (d, J=2.0 Hz, 1H, H-6), 6.40 (d, J=2.0 Hz, 1H, H-8), 3.80 (s, 3H, OCH$_3$), 3.79 (s, 3H, OCH$_3$); $^{13}$C NMR (400 MHz, MeOD): δ (ppm) 175.00 (s, C=O), 165.08 (s, C-7), 161.13 (s, C-5), 159.91 (s, C-9), 151.28 (d, C-2), 145.12 (s, C-3'), 145.0 (s, C-4'), 126.49 (s, C-3), 123.12 (s, C-1'), 120.50 (d, C-6'), 116.99 (d, C-2'), 110.00 (s, C-10), 114.48 (d, C-5'), 95.86 (d, C-6), 92.82 (d, C-8), 55.09 (q, 2×OCH$_3$). ESI-MS (positive): m/z calcd for C$_{17}$H$_{14}$O$_6$+H$^+$: 315.086300 [M+H]$^+$(monoisotopic mass). found: 315.086363.

Compound 1: Glabrescione B: 3-(3',4'-bis(3-methyl-but-2-enyloxy)phenyl)-5,7-dimethoxy-4H-chromen-4-one (1)

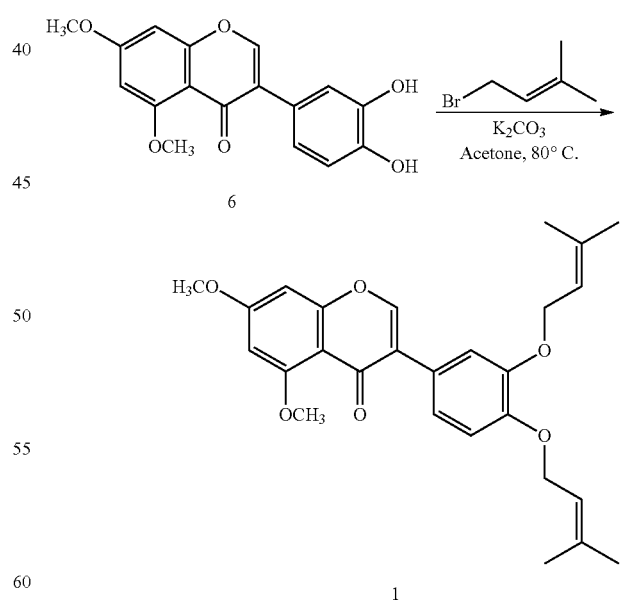

To a solution of 6 (61.8 mmol, 570 mg) in acetone (100 ml) was added K$_2$CO$_3$ (5.4 mmol, 7.4 g) and, after 10 minutes of stirring at room temperature, was added 3,3-dimethylallyl bromide (6.5 mmol, 968 mg). Then, the mixture was stirred at 80° C. overnight. Afterwards, the solvent was evaporated. The resulting solid was dissolved in EtOAc and extracted with water. The combined organic layers were dried over $Na_2SO_4$ and finally concentrated under reduced pressure. The crude was purified by column chromatography using hexane-EtOAc as eluent to obtain compound 1 as white powder. The powder was recrystallized from hexane resulting with white crystals.

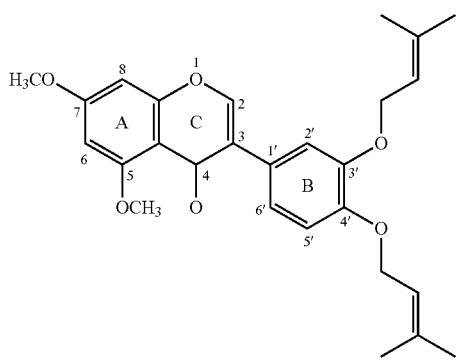

3-(3',4'-bis(3-methylbut-2-enyloxy)phenyl)-5,7-dimethoxy-4H-chromen-4-one (1)

White solid, (696 mg) 86% yield. Mp 102-104° C. $^1H$ NMR (400 MHz, Acetone-$d_6$): δ (ppm) 7.94 (s, 1H, H-2), 7.16 (d, 1H, J=1.6 Hz, H-2'), 6.99 (dd, 1H, J=8.0 Hz and 1.6 Hz, H-6'), 6.89 (d, 1H, J=8.0 Hz H-5'), 6.50 (d, 1H, J=2.0 Hz, H-8), 6.42 (d, 1H, J=2.0 Hz, H-6), 5.43 (m, 2H, 2×=CH), 4.51 (d, J=6.8 Hz, 4H, 2×$OCH_2$), 3.86 (s, 3H, $OCH_3$), 3.81 (s, 3H, $OCH_3$), 1.70 (s, 6H, 2×$CH_3$), 1.67 (s, 6H, 2×$CH_3$); $^{13}C$ NMR (400 MHz, $CDCl_3$): δ (ppm) 175.59 (s, C=O), 164.02 (s, C-7), 161.23 (s, C-5), 159.67 (s, C-9), 150.20 (d, C-2), 148.89 (s, C-3'), 148.51 (s, C-4'), 136.85 (s, 2×C=), 126.50 (s, C-3), 125.00 (s, C-1'), 121.44 (d, C-6'), 120.65 (d, 2×=CH), 115.50 (d, C-2'), 110.00 (s, C-10), 114.00 (d, C-5'), 96.47 (d, C-6), 92.60 (d, C-8), 65.95 (t, 2×$OCH_2$), 56.44 (q, $OCH_3$), 55.93 (q, $OCH_3$), 25.62 (q, 2×$CH_3$), 18.13 (q, 2×$CH_3$). ESI-MS (positive): m/z calcd for $C_{27}H_{30}O_6$+$H^+$: 451.211500 [M+H]$^+$(monoisotopic mass). found: 451.211495.

The $^1$H-NMR data of this product were identical to an authentic sample of Glabrescione B.

Example n. 8: Chemical Synthesis of Compounds NT8, NT9, NT10 and NT11

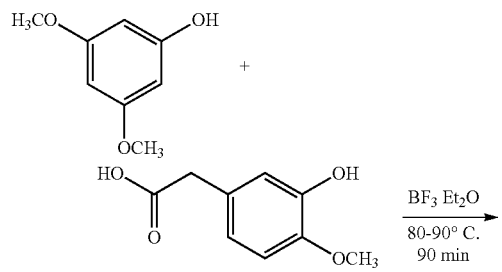

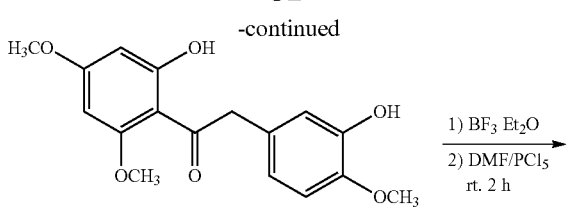

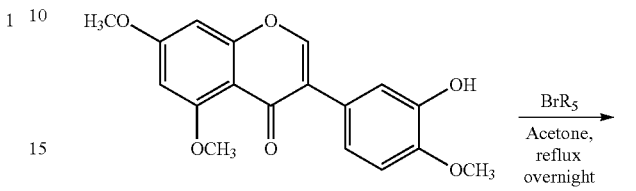

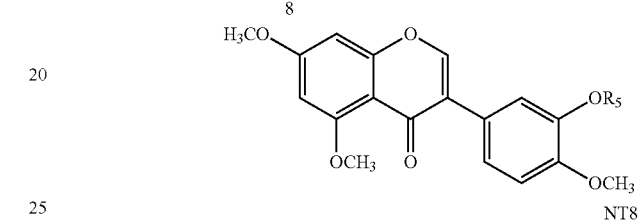

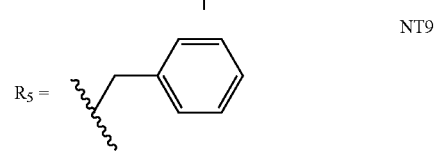

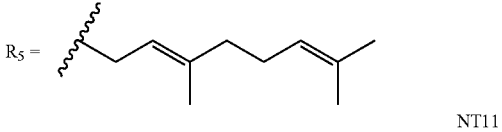

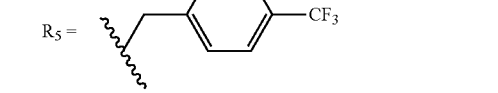

A mixture of 3,5-dimethoxyphenol (1.3 mmol, 463 mg) (SIGMA-ALDRICH 132632), 3,4-dihydroxyphenylacetic acid (2, 3 mmol, 504.5 mg) (SIGMA-ALDRICH 850217) and $BF_3.Et_2O$ (15.3 mmol, 1.94 ml) was stirred at 90° C. for 90 min under Argon. The reaction mixture was poured into 10% aqueous NaOAc solution (100 ml) and allowed to stand 4 h. The solution was extracted with EtOAc. The combined organic layers were washed with saturated solution of $NaHCO_3$, dried over $Na_2SO_4$ and finally concentrated under reduced pressure. The residue was purified by column chromatography using hexane-EtOAc mixture as eluent to obtain 1-(2-hydroxy-4,4-dimethoxy-phenyl)-2-(3-hydroxy-4-methoxy-phenyl)-ethanone 7. A mixture of 7 (3 mmol) and $BF_3.Et_2O$ (9 mmol, 1.2 mL) was cooled to 10° C. and DMF (4.6 ml) was added drop wise. In another flask, DMF (8 mL) was cooled to 10° C. and $PCl_5$ (4.5 mmol) was added. The mixture was then allowed to stand to 55° C. for 20 min. The light yellow colored solution containing N,N'-dimethyl (chloromethylene)ammonium chloride was then added to the above reaction mixture at 20-25° C. The mixture was stirred at r.t. for 2 h then poured into methanolic HCl (0.1N) and allowed to stand at 700 for 2 h. After removing the solvent the solution was extracted with EtOAc (3×100 mL) and the combined organic layer was washed with brine, dried over Na$_2$SO$_4$, and finally concentrated under reduced pressure. The residue was purified by column chromatography using hexane-EtOAc as eluent to give 3-(3'-hydroxy-4'-methoxy-phenyl)-5,7-dimethoxy-chromen-4-one 8.

To a solution of 8 (0.18 mmol, 60 mg) in acetone (5 ml) at 45° C. was added solid K$_2$CO$_3$ (8 eq). R$_5$Br (1.5 eq) was added drop wise to the mixture and stirred at 45° C. for 3 h. The progress of the reaction was monitored by thin layer chromatography (SIO$_2$ gel, developing solvent V exane:V EtOAc=3:7). When only one spot was on the TLC the reaction was quenched, extracted with EtOAc, the combined organic layer was dried over Na$_2$SO$_4$ and evaporated under reduced pressure.

3-[3'-(3-methyl-but-2-enyloxy)-4'-methoxyphenyl]-5,7-dimethoxy-4H-chromen-4-one (NT8)

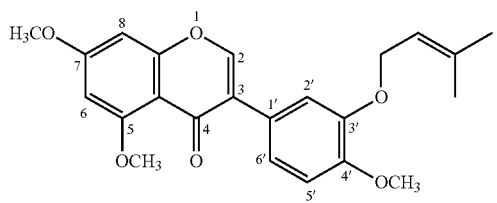

Yellow oil, 47% yield. $^1$H NMR (400 MHz, CDCl$_3$): δ (ppm) 7.76 (s, 1H, H-2), 7.22 (d, 1H, J=1.6 Hz, H-2'), 7.01 (dd, 1H, J=8 Hz and J=1.6 Hz, H-6'), 6.88 (d, 1H, J=8.4 Hz, H-5'), 6.44 (d, 1H, J=2 Hz, H-8), 6.37 (d, 1H, J=2 Hz, H-6), 5.55 (t, 1H, J=6.4 Hz, =CH), 4.59 (d, 2H, J=6.8 Hz, CH$_2$), 3.94 (s, 3H, OCH$_3$), 3.88 (s, 6H, 2×OCH$_3$), 1.76 (s, 3H, CH$_3$), 1.71 (s, 3H, CH$_3$).

3-(3'-Benzyloxy-4'-methoxyphenyl)-5,7-dimethoxy-4H-chromen-4-one (NT9)

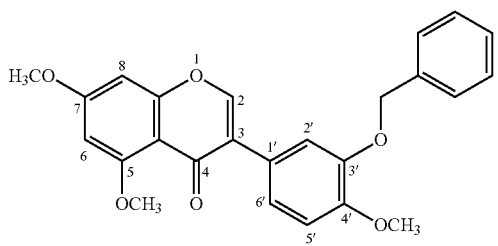

White powder, 44% yield. MP: 126° C. $^1$H NMR (400 MHz, CDCl$_3$): δ (ppm) 7.71 (s, 1H, H-2), 7.46 (dd, 2H, J=7.6 and J=1.6 Hz, ArH), 7.36 (t, 2H, J=7.6 Hz, ArH) 7.31 (dd, 1H, J=7.2 and J=2 Hz, ArH), 7.29 (d, 1H, J=2 Hz, H-2') 7.07 (dd, 1H, J=8.4 and J=2 Hz, H-6'), 6.92 (d, 1H, J=8.4 Hz, H-5'), 6.44 (d, 1H, J=2 Hz, H-8), 6.37 (d, 1H, J=2 Hz, H-6), 5.17 (s, 2H, OCH$_2$), 3.95 (s, 3H, OCH$_3$), 3.90 (s, 3H, OCH$_3$), 3.89 (s, 3H, OCH$_3$).

3-[3-(3,7-Dimethyl-octa-2,6-dienyloxy)-4-methoxyphenyl]-5,7-dimethoxy-chromen-4-one (NT10)

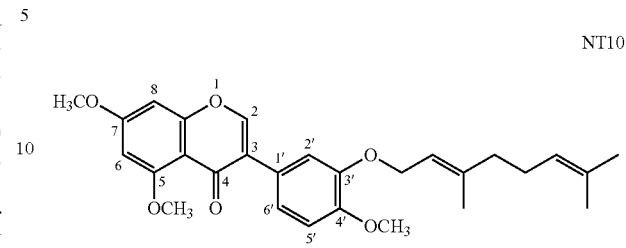

White powder, 44% yield $^1$H NMR (400 MHz, CDCl$_3$): δ (ppm) 7.76 (s, 1H, H-2), 7.22 (d, 1H, J=1.6 Hz, H-2'), 7.01 (dd, 1H, J=8 Hz and J=1.6 Hz, H-6'), 6.88 (d, 1H, J=8. Hz, H-5'), 6.44 (d, 1H, J=2 Hz, H-8), 6.37 (d, 1H, J=2 Hz, H-6), 5.55 (t, 1H, J=6.4 Hz, =CH), 5.39 (t, 1H, J=7 Hz, =CH), 4.59 (d, 2H, J=6.4 Hz, OCH$_2$), 3.94 (s, 3H, OCH$_3$), 3.88 (s, 6H, 2×OCH$_3$), 2.14 (t, 2H, J=6.9 Hz CH$_2$), 2.00 (q, 2H, J=7 Hz, CH$_2$—CH$_2$—CH=), 1.76 (s, 3H, CH$_3$), 1.71 (s, 6H, 2×CH$_3$).

5,7-Dimethoxy-3-[4-methoxy-3-(4-trifluoromethyl-benzyloxy)-phenyl]-chromen-4-one (NT11)

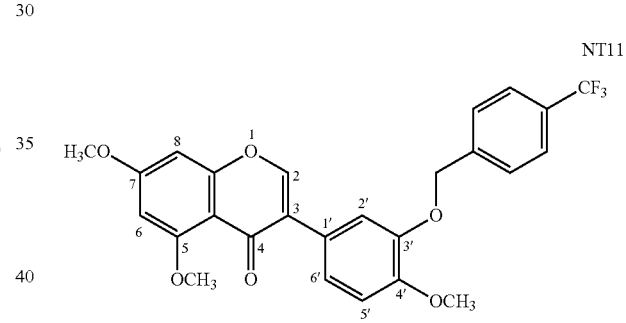

White powder, 78% yield. MP: 128.6-129.1° C. $^1$H NMR (400 MHz, acetone-d6): δ (ppm) 8.01 (s, 1H, H-2), 7.78 (m, 4H, ArH), 7.36 (d, 1H, J=2.1 Hz, H-2'), 7.15 (dd, 1H, J=8.3 Hz and J=2.1 Hz, H-6'), 7.02 (d, 1H, J=8.4, H-5'), 6.57 (d, 1H, J=2.3 Hz, H-8), 6.49 (d, 1H, J=2.3 Hz, H-6), 5.27 (s, 2H, OCH$_2$), 3.93 (s, 3H, OCH$_3$), 3.89 (s, 3H, OCH$_3$), 3.88 (s, 3H, OCH$_3$).

Example n. 9: Chemical Synthesis of Compounds NT12, NT13, NT14 and NT15

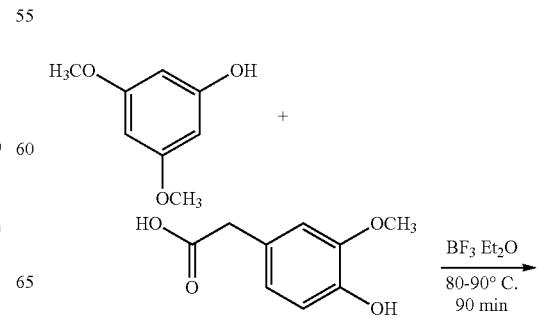

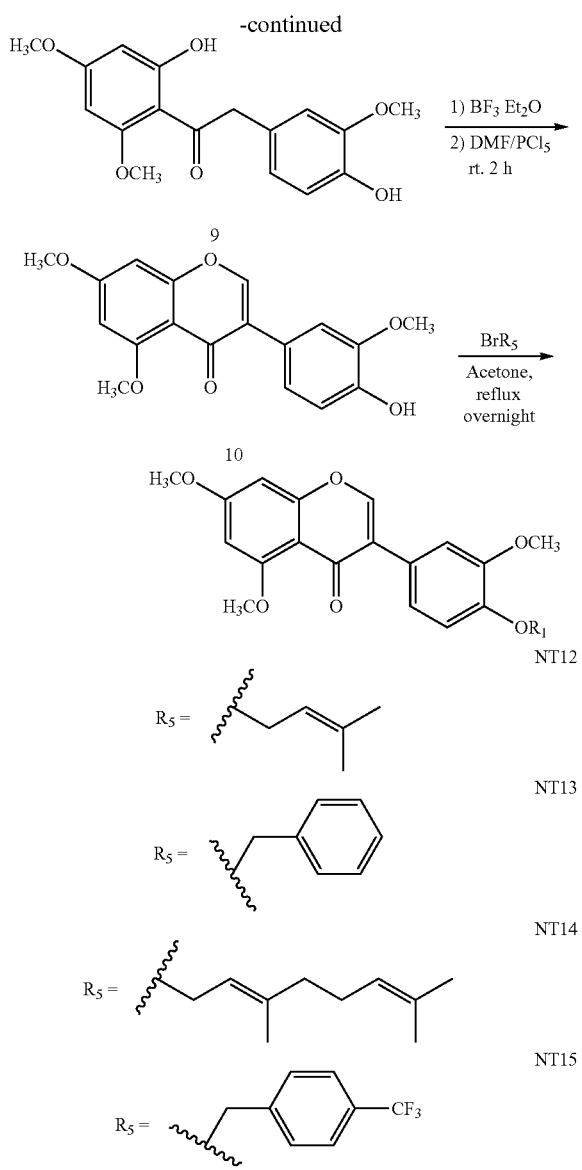

extracted with EtOAc (3×100 mL) and the combined organic layer was washed with brine, dried over $Na_2SO_4$, and finally concentrated under reduced pressure. The residue was purified by column chromatography using hexane-EtOAc as eluent to give 10.

To a solution of 10 (0.18 mmol, 60 mg) in acetone (5 ml) at 45° C. was added solid $K_2CO_3$ (8 eq). $R_5Br$ (1.5 eq) was added drop wise to the mixture and stirred at 45° C. for 3 h. The progress of the reaction was monitored by thin layer chromatography ($SIO_2$ gel, developing solvent V exane:V EtOAc=3:7). When only one spot was on the TLC the reaction was quenched, extracted with EtOAc, the combined organic layer was dried over $Na_2SO_4$ and evaporated under reduced pressure.

5,7-Dimethoxy-3-[3'-methoxy-4'-(3-methyl-but-2-enyloxy)-phenyl]-chromen-4-one (NT12)

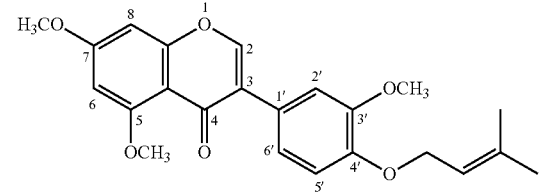

Yellow powder, 45% yield. MP: 130.7-131.8° C. $^1H$ NMR (400 MHz, $CDCl_3$): δ (ppm) 7.78 (s, 1H, H-2), 7.23 (d, 1H, J=2.0 Hz, H-2'), 6.96 (dd, 1H, J=8.0 and J=2.0 Hz, H-6'), 6.88 (d, 1H, J=8.0 Hz, H-5'), 6.44 (d, 1H, J=2.4 Hz, H-8), 6.37 (d, 1H, J=2.4 Hz, H-6), 5.53 (m, 1H, =CH), 4.60 (d, 2H, J=6.8 Hz, $OCH_2$), 3.94 (s, 3H, $OCH_3$), 3.89 (s, 6H, 2×$OCH_3$), 1.77 (s, 3H, $CH_3$), 1.73 (s, 3H, $CH_3$).

3-(4-Benzyloxy-3-methoxy-phenyl)-5,7-dimethoxy-chromen-4-one (6b) (NT13)

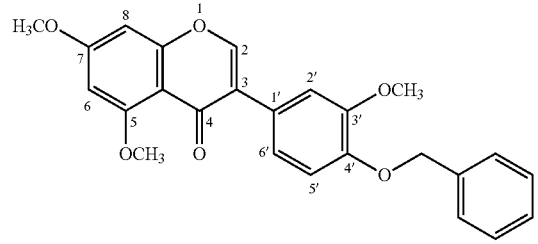

A mixture of 3,5-dimethoxyphenol (1.3 mmol, 463 mg), 3,4-dihydroxyphenylacetic acid (2, 3 mmol, 504.5 mg) and $BF_3 \cdot Et_2O$ (15.3 mmol, 1.94 ml) was stirred at 90° C. for 90 min under Argon. The reaction mixture was poured into 10% aqueous NaOAc solution (100 ml) and allowed to stand 4 h. The solution was extracted with EtOAc. The combined organic layers were washed with saturated solution of $NaHCO_3$, dried over $Na_2SO_4$ and finally concentrated under reduced pressure. The residue was purified by column chromatography using hexane-EtOAc mixture as eluent to obtain 9.

A mixture of 9 (3 mmol) and $BF_3 \cdot Et_2O$ (9 mmol, 1.2 mL) was cooled to 10° C. and DMF (4.6 ml) was added drop wise. In another flask, DMF (8 mL) was cooled to 10° C. and $PCl_5$ (4.5 mmol) was added. The mixture was then allowed to stand to 55° C. for 20 min. The light yellow colored solution containing N,N'-dimethyl(chloromethylene)ammonium chloride was then added to the above reaction mixture at 20-25° C. The mixture was stirred at r.t. for 2 h then poured into methanolic HCl (0.1N) and allowed to stand at 700 for 2 h. After removing the solvent the solution was White powder, 56% yield. MP: 142.8-143.7° C. $^1H$ NMR (400 MHz, $CDCl_3$): δ (ppm) 7.77 (s, 1H, H-2), 7.45 (dd, 2H, J=8.0 Hz and J=2.0 Hz, ArH), 7.37 (t, 2H, J=8.0 Hz, ArH), 7.31 (dd, 1H, J=8 Hz and J=1.6 Hz, ArH), 7.30 (d, 1H, J=2.0 Hz, H-2'), 6.89 (m, 2H, H-6' and H-5'), 6.45 (d, 1H, J=2 Hz, H-8), 6.38 (d, 1H, J=2 Hz, H-6), 5.19 (s, 1H, $OCH_2$), 3.94 (s, 3H, $OCH_3$), 3.93 (s, 3H, $OCH_3$), 3.90 (s, 3H, $OCH_3$)

3-[4'-(3,7-Dimethyl-octa-2,6-dienyloxy)-3'-methoxy-phenyl]-5,7-dimethoxy-chromen-4-one (NT14)

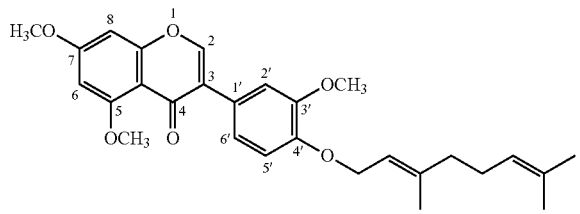

NT14

White powder, 44% yield $^1$H NMR (400 MHz, CDCl$_3$): δ (ppm) 7.76 (s, 1H, H-2), 7.22 (d, 1H, J=1.6 Hz, H-2'), 7.01 (dd, 1H, J=8 Hz and J=1.6 Hz, H-6'), 6.88 (d, 1H, J=8 Hz, H-5'), 6.44 (d, 1H, J=2 Hz, H-8), 6.37 (d, 1H, J=2 Hz, H-6), 5.42 (t, 1H, J=6.4 Hz, =CH), 5.12 (t, 1H, J=7 Hz, =CH), 4.41 (d, 2H, J=6.4 Hz, OCH$_2$), 3.94 (s, 3H, OCH$_3$), 3.90 (s, 3H, OCH$_3$), 3.88 (s, 3H, OCH$_3$), 2.14 (t, 2H, J=6.9 Hz CH$_2$), 2.00 (q, 2H, J=7 Hz, CH$_2$—CH$_2$—CH=), 1.76 (s, 3H, CH$_3$), 1.71 (s, 6H, 2×CH$_3$).

5,7-Dimethoxy-3-[3-methoxy-4-(4-trifluoromethyl-benzyloxy)-phenyl]-chromen-4-one (NT15)

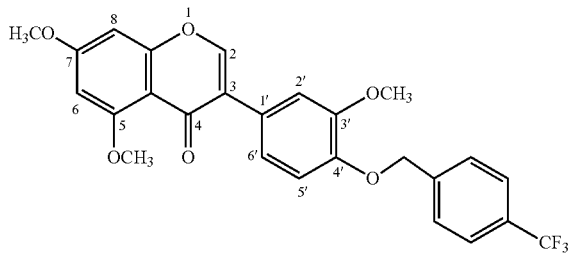

NT15

White powder, 25% yield. MP: 128.4-130.2° C. $^1$H NMR (400 MHz, acetone-d6): δ (ppm) 8.04 (s, 1H, H-2), 7.76 (m, 4H, ArH), 7.29 (d, 1H, J=2.1 Hz, H-2'), 7.06 (m, 2H, H-5' and H-6'), 6.58 (d, 1H, J=2 Hz, H-8), 6.50 (d, 1H, J=2 Hz, H-6), 5.28 (s, 2H, OCH$_2$), 3.94 (s, 3H, OCH$_3$), 3.89 (s, 6H, 2×OCH$_3$).

Example n.10: Preparation of the Virtual Library

The in house unique library was composed of 816 different natural products. Single molecular entries were generated in SMILES format and then transformed in the 3D SDF format. The LigPrep application of the Schrodinger Maestro suite was used for ionizing compounds at pH=7.5±1, for generating tautomers and for energy minimization with the OPLS2005 force field (Jorgensen, Maxwell et al. 1996). Ionization and tautomerization states endowed with a normalized probability higher than 0.6 were retained in the library. After this step the library was composed of 1111 individual entries. The Qik-Prop application of the Maestro suite was used to predict chemical and chemico-physical features of all compounds. The conformational analysis was carried out by means of the "Build 3D Database" protocol of Discovery Studio 2.5 using the CAESAR conformation method with default options and keeping up to 600 conformers for each ligand.

Example n.11: Generation of Pharmacophore Models

A training set of 9 potent SMO antagonists was used to generate pharmacophore models according with a ligand-based procedure. The "Common Feature Pharmacophore Generation" protocol implemented in Discovery Studio 2.5 from Accelrys was used. Up to 20 pharmacophores were generated, composed by a maximum of 10 features. The minimum inter-feature distance was set at 2.0 Å while the number of leads that may miss was kept at the default value (1). Conformational analysis of the training set was carried out with the CAESAR method. The maximum number of omitted features during the alignment of the training set to pharmacophores was set at 1. This procedure generated twenty pharmacophores (maximum allowed value, according to custom settings). The six top-ranking pharmacophores are divided into two groups, based on the pharmacophoric feature composition. Type1 pharmacophores have three hydrogen bond acceptor (HBA) and three hydrophobic (HYD) features. Type2 pharmacophores have three HBA, two HYD and a hydrogen bond donor (HBD) features (FIG. 1). Coordinates of pharmacophores and inter-feature distances are given in Tables 1 and 2 for the representative Type1 pharmacophore model (3 HYD; 3 HBA) and in Tables 3 and 4 for the representative Type2 pharmacophore (2 HYD; 1 HBD; 3 HBA).

TABLE 1

Coordinates of the representative pharmacophore Type 1.

| Feature | x | y | z | Radius (Å) |
|---|---|---|---|---|
| HYD1 | −5.940 | 2.940 | 0.780 | 1.7 |
| HYD2 | 4.000 | 2.360 | −1.260 | 1.7 |
| HYD3 | 5.420 | −2.960 | −0.980 | 1.7 |
| HBA1-tail | −1.998 | 3.801 | 0.538 | 1.7 |
| HBA1-head | −0.520 | 6.360 | 1.180 | 2.3 |
| HBA2-tail | −6.760 | 5.444 | 1.054 | 1.7 |
| HBA2-head | −9.760 | 5.440 | 1.140 | 2.3 |
| HBA3-tail | 2.885 | −1.548 | 0.149 | 1.7 |
| HBA3-head | 1.000 | −1.980 | 2.460 | 2.3 |

HYD: Hydrophoic feature; HBA: H-Bond Acceptor feature.
Coordinates are in Å.

TABLE 2

Distance matrix of the representative pharmacophore Type1. For HBA features, distances have been calculated referring to the tail. Distances are expressed in Å.

| Feature | HYD1 | HYD2 | HYD3 | HBA1 | HBA2 | HBA3 |
|---|---|---|---|---|---|---|
| HYD1 | — | 10.164 | 12.921 | 4.042 | 2.649 | 9.921 |
| HYD2 | — | — | 5.513 | 6.425 | 11.430 | 4.301 |
| HYD3 | — | — | — | 10.151 | 14.937 | 3.114 |
| HBA1 | — | — | — | — | 5.064 | 7.253 |
| HBA2 | — | — | — | — | — | 11.947 |
| HBA3 | — | — | — | — | — | — |

TABLE 3

Coordinates of the representative pharmacophore Type 2.

| Feature | x | y | z | Radius (Å) |
|---|---|---|---|---|
| HYD1 | −5.620 | −2.740 | 0.900 | 1.7 |
| HYD2 | 4.740 | 2.800 | 0.280 | 1.7 |
| HBD-tail | −3.007 | −3.615 | 0.875 | 1.7 |
| HBD-head | −2.040 | −5.900 | 2.640 | 2.3 |
| HBA1-tail | −3.058 | −1.953 | −0.696 | 1.7 |
| HBA1-head | −2.220 | −0.080 | −2.900 | 2.3 |
| HBA2-tail | 2.512 | 4.671 | 0.244 | 1.7 |
| HBA2-head | −0.440 | 4.120 | 0.520 | 2.3 |
| HBA3-tail | 4.167 | −1.126 | −0.138 | 1.7 |
| HBA3-head | 6.120 | −3.440 | −0.340 | 2.3 |

HYD: Hydrophoic feature; HBA: H-Bond Acceptor feature.
Coordinates are in Å.

TABLE 4

Distance matrix of the representative pharmacophore Type2. For HBA and HBD features, distances have been calculated referring to the tail. Distances are expressed in Å.

| Feature | HYD1 | HYD2 | HYD3 | HBA1 | HBA2 | HBA3 |
|---|---|---|---|---|---|---|
| HYD1 | — | 11.765 | 2.756 | 3.119 | 11.022 | 9.973 |
| HYD2 | — | — | 10.076 | 9.184 | 2.910 | 3.990 |
| HBD | — | — | — | 2.288 | 9.976 | 7.661 |
| HBA1 | — | — | — | — | 8.706 | 7.294 |
| HBA2 | — | — | — | — | — | 6.041 |
| HBA3 | — | — | — | — | — | — |

Example n.12: Pharmacophoric Screening

The in house unique library of natural products, generated as described in example n.10 was screened through the six pharmacophores. First, the "Search 3D Database" protocol implemented in Discovery Studio 2.5 was used to select molecules able to map the pharmacophores. The "Best" search method was used, which perform a flexible fit of the ligand conformations against the pharmacophore. The "Ligand Pharmacophore Mapping" protocol was subsequently used to fit the selected conformations to the pharmacophores and to calculate the FitValue. No omitted features were allowed during ligand fitting to pharmacophores. The flexible fitting method was used, which permit a slight modification of each ligand conformation to better fit the pharmacophore.

By pharmacophore screening, three groups of molecules were selected from the initial library: 1) ligands that map all pharmacophores; 2) ligands that map only type1 pharmacophores and 3) ligands that map only type2 pharmacophores. With the aim of prioritizing small molecular compounds, the Ligand Efficiency (LE) was further calculated for each compound as the ratio between its FitValue and the number of heavy atoms (LE=FitValue/no. heavy atoms). 16 natural compounds endowed with the highest LE were selected for in vitro studies (see above).

Example n.13: Structure-Based Virtual Screening

Initial coordinates of the Gli1-ZF/DNA complex were retrieved from the Protein Data Bank under the PDB accession code 2GLI. Coordinates of crystal water molecules were manually removed from the complex, while cobalt ions were manually replaced with zinc ions within the coordination system of each zinc finger. The Amber11 program (Case, Cheatham et al. 2011) was used for generating MD trajectories and performing energy calculations. The AmberTools1.5 software was used for preparing input coordinates and topology files, and for performing preliminary analysis on MD trajectories by the ptraj and cpptraj modules. The ff99bsc0 and General Amber (GAFF) force fields were used for parameterizing protein and ligands, respectively. Zinc ions were treated following a bound approach; parameters for the zinc ion and zinc-coordinating residues were adapted from a previous QM calculation (Mori, Dietrich et al. 2010). The Gli1-ZF/DNA complex was solvated in a rectilinear box of explicit water molecules, buffering 8 Å from the macromolecular system. The TIP3P water model was used. The total charge of the system was neutralized by the addition of sodium counterions (Na+). The solvated macromolecular system was first energy minimized as follows: the water solvent and counterions were first minimized for 250 steps by using a steepest descent algorithm (SD) and for 750 steps by using a conjugate gradient algorithm (CG), while keeping the Gli1-ZF/DNA coordinates as frozen; then, the solvated system was energy minimized for 1000 steps SD and further 4000 steps CG without positional restraints. Before the final production of trajectories, the energy minimized system was gradually heated from 0 to 300 K for 50 µs using the Langevin control of the temperature at constant pressure and constraining the Gli1-ZF backbone and the DNA phosphate backbone with a harmonic force constant of 5.0 kcal·mol$^{-1}$·Å$^{-2}$. Then, the density of the system was equilibrated for 50 µs, by applying the same constraints mask used in the heating step. Restrained MD trajectory were produced for 3 ns while the force constant applied to Glil-ZF and DNA backbone was gradually decreasing from 5 to 2 to 1 kcal·mol$^{-1}$·Å$^{-2}$ every 1 ns. After this step, unrestrained MD trajectories were generated for 20 ns by using SANDER. During all MD simulations, a time step of 0.001 µs was used. A representative Gli1-ZF structure was extracted from MD trajectories and used as rigid receptor for docking simulations. The GOLD docking program (version 5.0.1) was used to dock the in house library towards the binding site centered on the side chain of Thr374 and having a radius of 18 Å. The GoldScore function was used whit Genetic Algorithm (GA) efficacy set at 150% and generating 50 runs for ligands, while other parameters were kept at their default values. Docking poses were rescored by means of the MM-GB SA method implemented in Amber11.

Example n.14

NMR experiments were carried out to probe the direct interaction of Glabrescione B to Gli1-ZF and to support computational and biological data.

A sample of Glabrescione B 0.412 mM in DMSO-d$_6$ was prepared and added to 20 µL of a solution of Gli1-GST (Glutathione S-transferase) fusion protein at 5 µg/µL, providing a molar ratio of Glabrescione B/Gli1-GST of 150:1. Relaxation speeds of Glabrescione B protons were monitored via NMR (600 MHz), results are showed in Table 5. In experimental conditions, Glabrescione B protons experiencing the most significant perturbation of the relaxation speed, due to the presence of Gli1-GST, belong to the ring A of the isoflavone nucleus, namely aromatic protons $H_1$, $H_3$ and those belonging to methoxyl groups 2' and 4'. In addition, protons $H_{11}$ and $H_{15}$ belonging to the ring C showed a significant perturbation of the relaxation speed in presence of Gli1, while $H_8$ showed only a small variation.

It is worth noting that the same experiments were conducted also in presence of GST alone to monitor the influence of GST in the fusion protein Gli1-GST to the binding of Glabrescione B. Results showed that the normalized perturbation of the relaxation speed is significantly lower than that observed in presence of Gli1-GST (Table 5) and suggested that Glabrescione B interacts most strongly with Gli1 than GST.

TABELLA 5

Normalized relaxation speed ($\Delta R/R_f$) of Glabrescione B protons (0.412 mM) in presence of Gli1-GST and GST alone.

| proton | GlaB $R_f^{ms}$ (S$^{-1}$) | GlaB:Gli1-GST 1:150 $\Delta R/R_f$ | GlaB:GST 1:150 $\Delta R/R_f$ |
|---|---|---|---|
| 1 | 0.41 | 0.341 | 0.024 |
| 2' | 1.20 | 0.267 | 0.058 |
| 3 | 0.63 | 0.206 | 0.100 |
| 4' | 1.39 | 0.482 | 0 |
| 8 | 0.36 | 0.028 | 0 |
| 11 | 0.63 | 0.286 | n.d. |
| 12 | 0.89 | 0 | 0.034 |
| 15 | 0.76 | 0.329 | 0.138 |
| 19 | 0.85 | 0 | 0 |

Moreover, Glabrescione B protons involved in binding to GST are significantly different from those involved in binding to Gli1.

Finally, since Gli1 is a zinc binding protein, it was monitored via NMR the direct interaction between Glabrescione B and $Zn^{2+}$, showing that the molecule is not capable of binding to the metal ions.

Example n.15

Since Glabrescione B was the most potent Hh inhibitor identified by the screening, a number of Glabrescione B analogues (namely NT8, NT9, NT10, NT11, NT12, NT13, NT14 and NT15) were synthesized and tested in vitro to improve inhibitory potency against the Hh pathway and to afford Structure-Activity Relationships (SAR) for the congeneric series (see examples 8 and 9). Evaluation of the Hh inhibitory activity of these molecules at 5 μM was preliminarily conducted in vitro on Shh Light II cells (see example 2). Preliminary results showed that some of these molecules were at least as active as Glabrescione B, with NT8 and NT9 being more potent than Glabrescione B (see FIG. 19).

BIBLIOGRAPHY

Ahn, S. and A. L. Joyner (2005). *Nature* 437(7060): 894-897.
Aszterbaum, M., et al., (1999). *Nat Med* 5: 1285-1291.
Atwood, S. X. Lynn, A., Chang, S. and Oro, A. E. (2012). *J. Cell Biol.* 199 (2):193-197.
Barnum, D., J. et al. (1996). *J Chem Inf Comput Sci* 36(3): 563-571.
Biegasiewicz, K. F., et al., (2010). *Tetrahedron Letters* 51(33): 4408-4410.
Buonamici, S., et al., (2010). *Sci Transl Med* 2(51): 51ra70.
Case D. A., et al., AMBER 11, University of California, San Francisco. (2011).
Clement, V., et al. (2007). *Curr Biol* 17(2): 165-172.
Chen, J. K., et al. (2002). *PNAS,* 99(22): 14071-14076.
Dahlen A, et al. (2004) *Am J Pathol* 164:1645-1653.
Dahmane, N. and A. Ruiz i Altaba (1999). *Development* 126(14): 3089-3100.
De Smaele, E., E. Ferretti and A. Gulino (2010). *Curr Opin Investig Drugs* 11(6): 707-718.
Delle Monache, F.; et al. (1977). *Gazzetta Chimica Italiana* 107(7-8): 403-407.
Di Marcotullio, L., et al. (2006). *Mol Neurobiol* 34(3): 193-204.
Di Marcotullio L, et al. (2011). *Oncogene* 30, 65-76.
Dijkgraaf, G. J., et al. (2011). *Cancer Res* 71(2): 435-444.
Eberl, M., et al. (2012). *EMBO Mol Med* 4:218-233.
Ellison, D. (2002). *Neuropathol Appl Neurobiol* 28(4): 257-282.
Epstein, E. H. (2008). *Nat. Rev. Cancer.* 8, 743-754.
Everett, L., Crabb, D. W. (1999). *J. Steroid Biochem Mol Biol,* 70(4-6):197-201.
Goodrich, L. V., et al. (1997). *Science* 277(5329): 1109-1113.
Hallahan, A. R., et al. (2004). *Cancer Res* 64(21): 7794-7800.
Ingham, P. W. and M. Placzek (2006). *Nat Rev Genet* 7(11): 841-850.
Jorgensen, W. L., et al. (1996). *Journal of the American Chemical Society* 118(45): 11225-11236.
Kinzler K W, et al. (1987) *Science* 236:70-73.
Kogerman P, et al. (1999). *Nat Cell Biol* 1:312-319.
Lai, K., B. K. Kaspar, F. H. Gage and D. V. Schaffer (2003). *Nat Neurosci* 6(1): 21-27.
Lauth, M., Bergstrom, A., Shimokawa, T., and Toftgard R (2007). *PNAS* 104(20): 8455-8460
Machold, R., et al. (2003). *Neuron* 39(6): 937-950.
Manetti, F., et al. (2010). *Mol Pharmacol* 78(4): 658-665.
Mori, M., et al. *J Chem Inf Model* 50, 638-50 (2010).
Palma, V., et al. (2005). *Development* 132(2): 335-344.
Palma, V. and A. Ruiz i Altaba (2004). *Development* 131(2): 337-345.
Pavletich, N. P. & Pabo, C. O. (1993). *Science* 261, 1701-7.
Ruiz i Altaba, A., P. Sanchez and N. Dahmane (2002). *Nat Rev Cancer* 2(5): 361-372.
Stecca, B. and A. Ruiz i Altaba (2009). *EMBO J* 28(6): 663-676.
Sheng, T., et al. (2006). *J Biol Chem* 281, 9-12.
Svärd, J., et al. (2006). *Dev. Cell* 10, 187-197.
Taipale, J., et al. (2000). *Nature* 406(6799): 1005-1009.
Taylor, M. D., et al. (2002). *Nat Genet* 31(3): 306-310.
Teglund, S. and R. Toftgard (2010). *Biochim Biophys Acta* 1805(2): 181-208.
Tremblay, M. R., et al. (2009). *Expert Opin Ther Pat* 19(8): 1039-1056.
Verdonk, M. L., et al. (2003). *Proteins* 52, 609-23.
Wallace, V. A. (1999). *Curr Biol* 9(8): 445-448.
Wechsler-Reya, R. J. and M. P. Scott (1999). *Neuron* 22(1): 103-114.
Yauch, R. L., et al. (2009). *Science* 326(5952): 572-574.
Ye, Y. Q., et al. (2009). *Organic Letters* 11(21): 5074-5077.

The invention claimed is:

1. A method for the treatment of a Hedgehog (Hh)-dependent tumor pathology comprising:
   administering to a human subject needing inhibition of the Hedgehog (Hh)-dependent tumor pathology, an effective amount of the compound having general formula I,

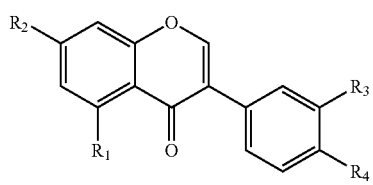
(I)

wherein:
$R_1$ is $OR_A$;
$R_2$ is $OR_B$;
wherein each of $R_A$ and $R_B$ is hydrogen or acyclic branched or straight, saturated or unsaturated aliphatic chain having from 1 to 10 carbon atoms;
$R_3$ is $OR_C$; and
$R_4$ is $OR_D$;
wherein each of $R_C$ and $R_D$ are methyl, ethyl, propyl, isopropyl, prenyl, geranyl, farnesyl or benzyl, wherein the phenyl of the benzyl group can be substituted by halogen, $C_1$-$C_6$ haloalkyl, $C_1$-$C_6$ haloalkoxy, $C_1$-$C_6$ alkoxy, $C_1$-$C_6$ alkylthio, amino, $C_1$-$C_6$ alkylamino, or $C_1$-$C_6$ dialkylamino, wherein the compound is an antagonist of Gli1 and the effective amount inhibits activation of Gli1 associated with the Hh-pathway.

2. The method of claim 1, wherein the Hh-dependent tumor pathology is resistant to a SMO inhibitor.

3. The method of claim 2, wherein the SMO inhibitor is vismodegib or NVP-LDE225.

4. The method of claim 1, wherein the Hh-dependent tumor pathology is selected from the group consisting of: medulloblastoma (MB), esophageal adenocarcinoma, basal cell carcinomas (BCCs), pancreatic, prostate, and small cell lung cancer.

5. The method of claim 1, wherein the Hh-dependent tumor pathology is present in a pediatric human subject.

6. The method of claim 1, wherein the compound is administered by intratumoral injection.

* * * * *